US010098215B2

(12) United States Patent
Nakahara et al.

(10) Patent No.: US 10,098,215 B2
(45) Date of Patent: Oct. 9, 2018

(54) X-RAY TUBE PREDICTIVE FAULT INDICATOR SENSING DEVICE, X-RAY TUBE PREDICTIVE FAULT INDICATOR SENSING METHOD, AND X-RAY IMAGING DEVICE

(71) Applicant: Hitachi, Ltd., Chiyoda-ku, Tokyo (JP)

(72) Inventors: Takashi Nakahara, Tokyo (JP); Shinya Yuda, Tokyo (JP); Takanori Aono, Tokyo (JP); Tetsu Inahara, Tokyo (JP); Yoshitaka Seki, Tokyo (JP); Kouji Akita, Tokyo (JP); Kiyomi Abe, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 176 days.

(21) Appl. No.: 15/313,982

(22) PCT Filed: Apr. 27, 2015

(86) PCT No.: PCT/JP2015/062738
§ 371 (c)(1),
(2) Date: Nov. 25, 2016

(87) PCT Pub. No.: WO2015/182317
PCT Pub. Date: Dec. 3, 2015

(65) Prior Publication Data
US 2017/0188443 A1 Jun. 29, 2017

(30) Foreign Application Priority Data
May 29, 2014 (JP) .................................. 2014-111711

(51) Int. Cl.
*H05G 1/26* (2006.01)
*H05G 1/54* (2006.01)
(Continued)

(52) U.S. Cl.
CPC ................. *H05G 1/26* (2013.01); *A61B 6/40* (2013.01); *A61B 6/586* (2013.01); *H05G 1/54* (2013.01); *A61B 6/03* (2013.01); *H01J 35/26* (2013.01)

(58) Field of Classification Search
CPC .... A61B 6/40; A61B 6/54; A61B 6/58; A61B 6/586; A61B 2560/00; A61B 2560/02;
(Continued)

(56) References Cited

FOREIGN PATENT DOCUMENTS

JP 2001-218762 A 8/2001
JP 2002-280195 A 9/2002
(Continued)

OTHER PUBLICATIONS

International Search Report (PCT/ISA/210) issued in PCT Application No. PCT/JP2015/062738 dated Jul. 28, 2015 with English translation (3 pages).
(Continued)

*Primary Examiner* — Anastasia Midkiff
(74) *Attorney, Agent, or Firm* — Crowell & Moring LLP

(57) ABSTRACT

A learning unit in learning mode generates a cluster from a cluster analysis of data formed from frequency constituent data and state data, obtained from a sensor unit. An abnormality calculation unit computes, as abnormalities, the minimum values among distances to surfaces of the clusters of the data formed from the frequency constituent data and the state data, obtained when in predictive fault indicator sensing mode. A predictive fault indicator determination unit determines a predictive fault indicator of an X-ray tube by comparing the abnormalities with a predetermined threshold.

9 Claims, 21 Drawing Sheets

(51) Int. Cl.
  *A61B 6/00*   (2006.01)
  *A61B 6/03*   (2006.01)
  *H01J 35/26*  (2006.01)

(58) Field of Classification Search
  CPC ..... A61B 2560/0266; A61B 2560/0276; H01J
      2237/00; H01J 2237/02; H01J 2237/0203;
      H05G 1/00; H05G 1/08; H05G 1/26;
      H05G 1/54; G01N 2223/00; G01N
      2223/30; G01N 2223/302–2223/306;
      G01T 7/00; G01T 7/005; G01T 7/12;
      G01T 7/125
  See application file for complete search history.

(56) References Cited

FOREIGN PATENT DOCUMENTS

| | | |
|---|---|---|
| JP | 2006-300896 A | 11/2006 |
| JP | 2009-11586 A | 1/2009 |
| JP | 2011-45626 A | 3/2011 |

OTHER PUBLICATIONS

Japanese-language Written Opinion (PCT/ISA/237) issued in PCT Application No. PCT/JP2015/062738 dated Jul. 28, 2015 (3 pages).

[Fig. 1]
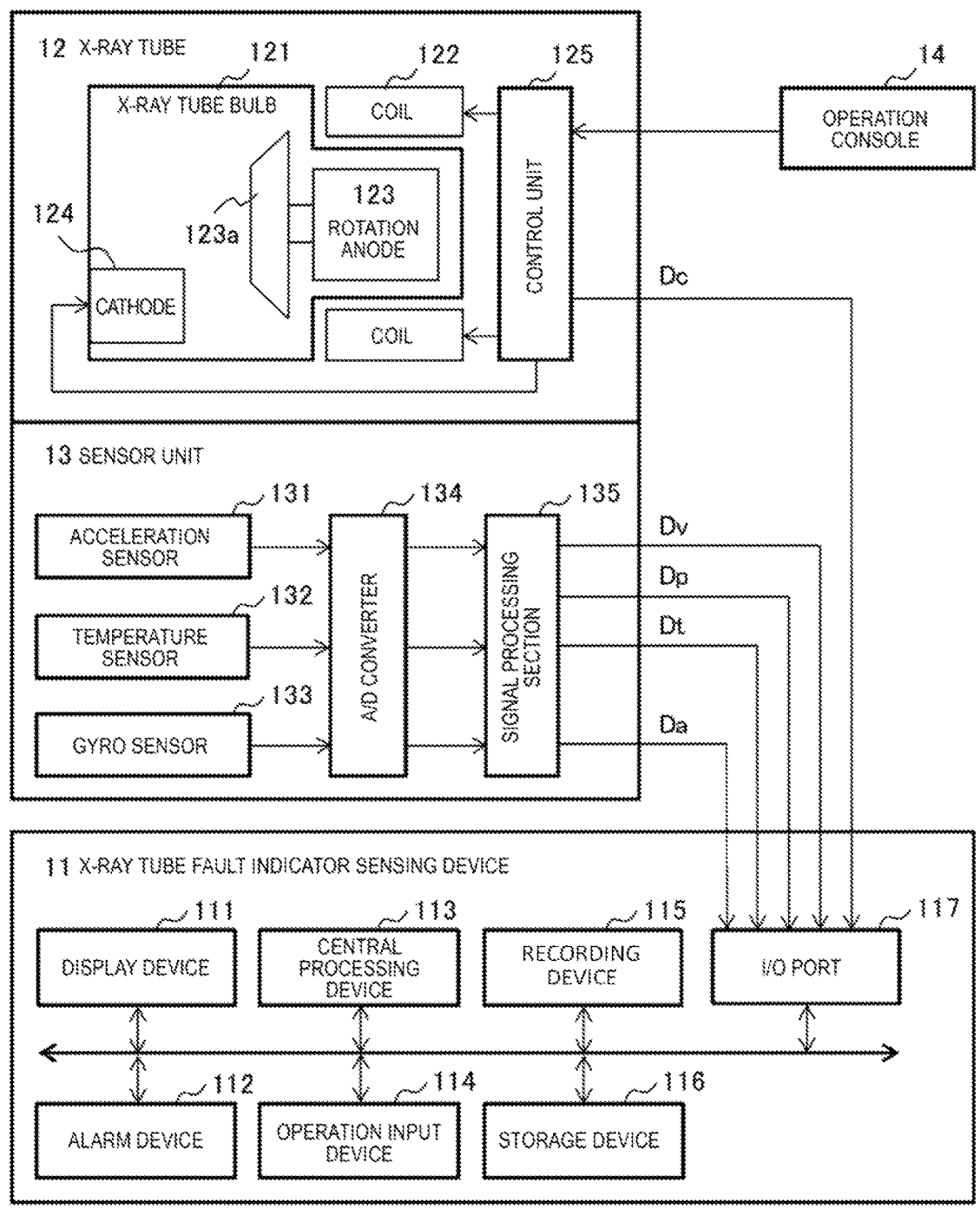

[Fig. 2]
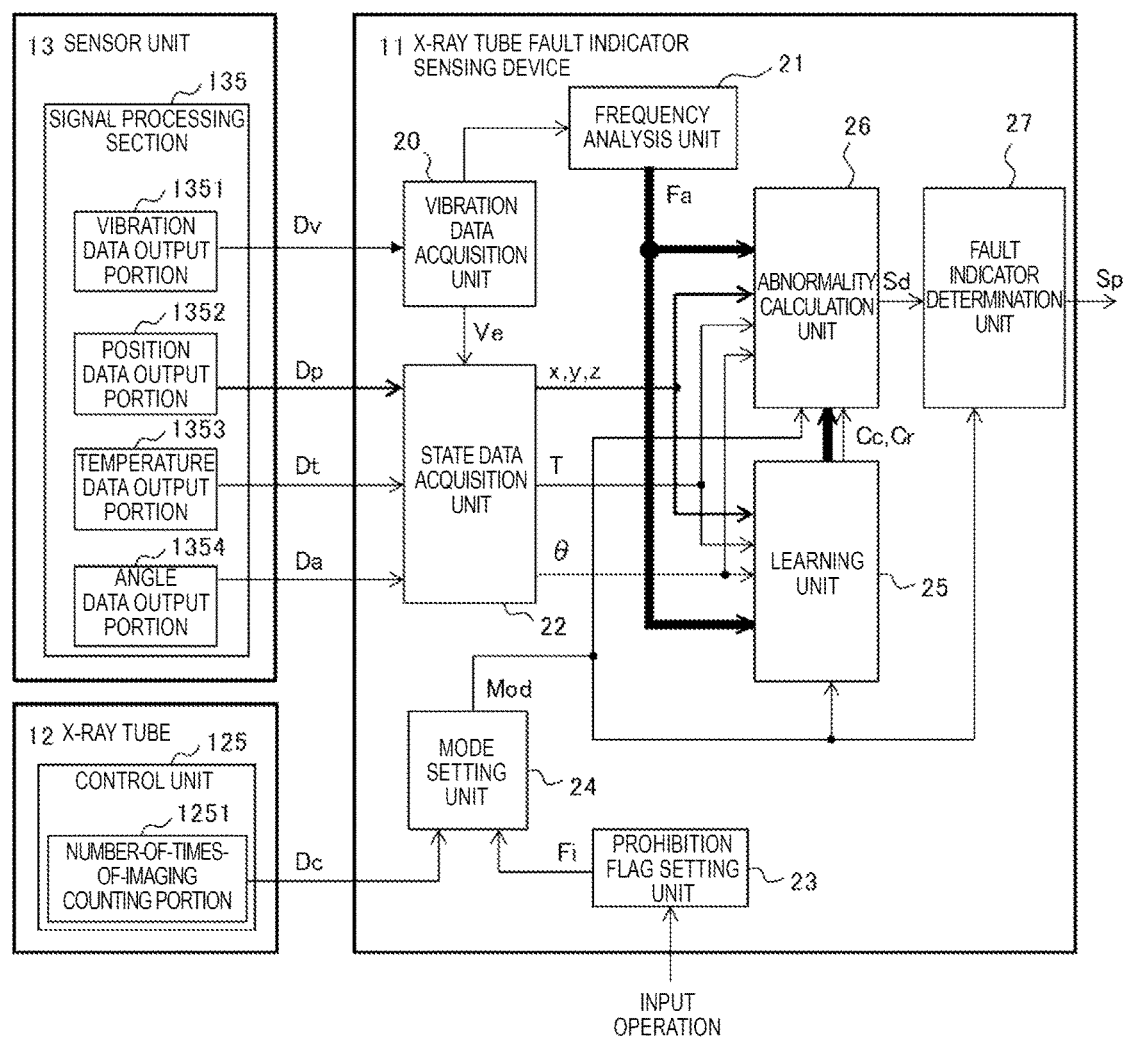

[Fig. 3]
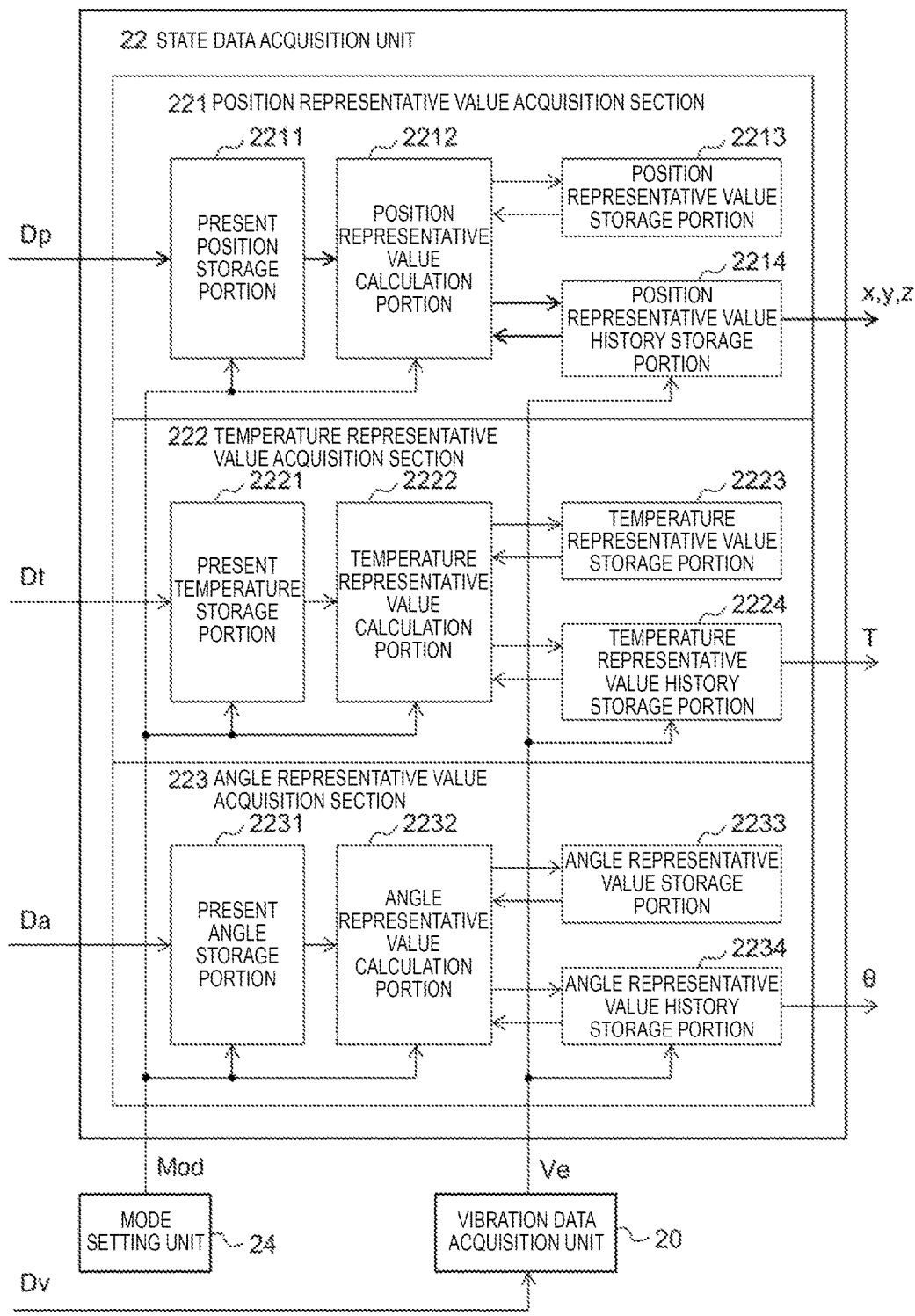

[Fig. 4]
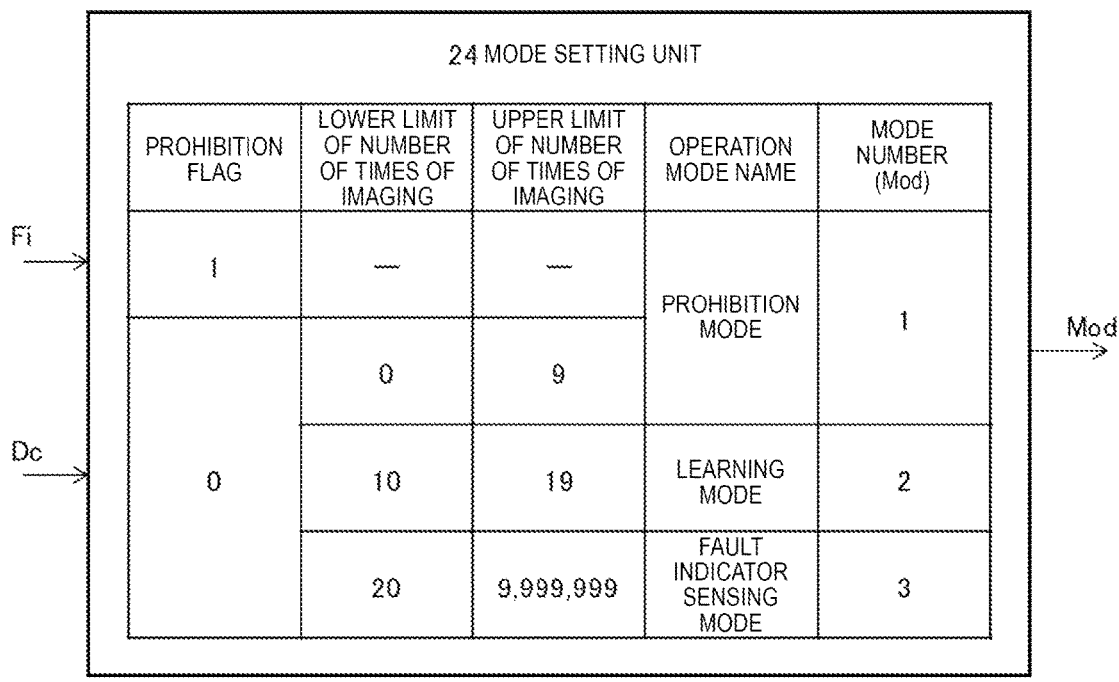

[Fig. 5]
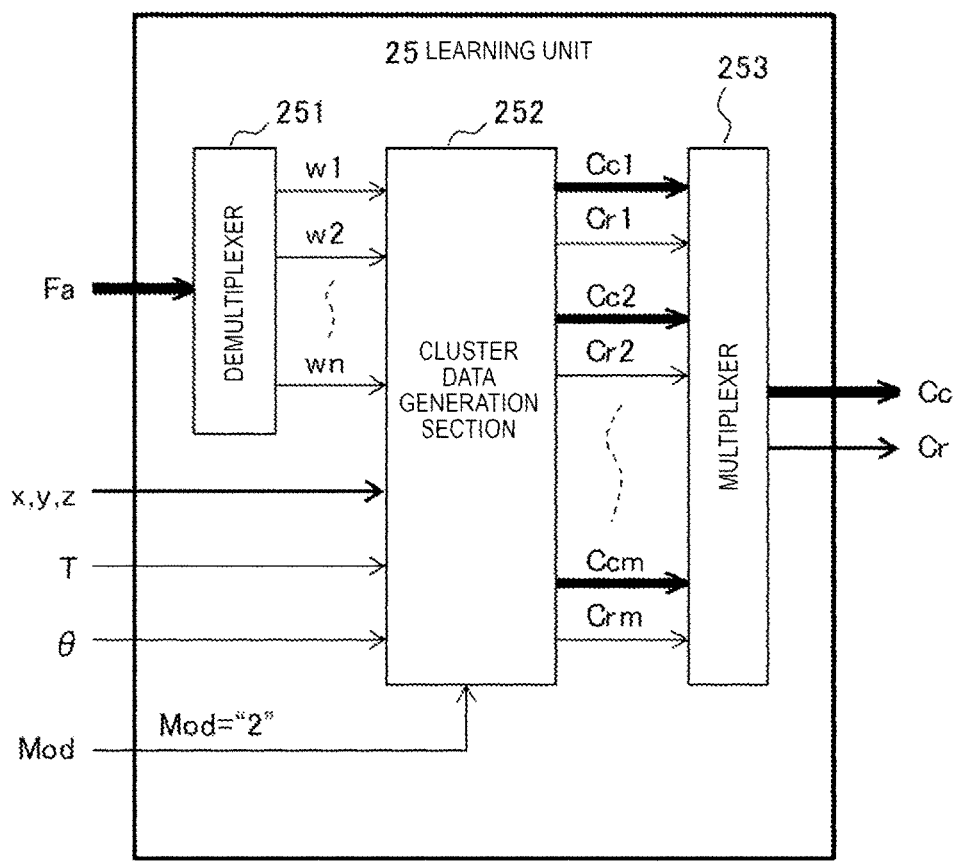

[Fig. 6]
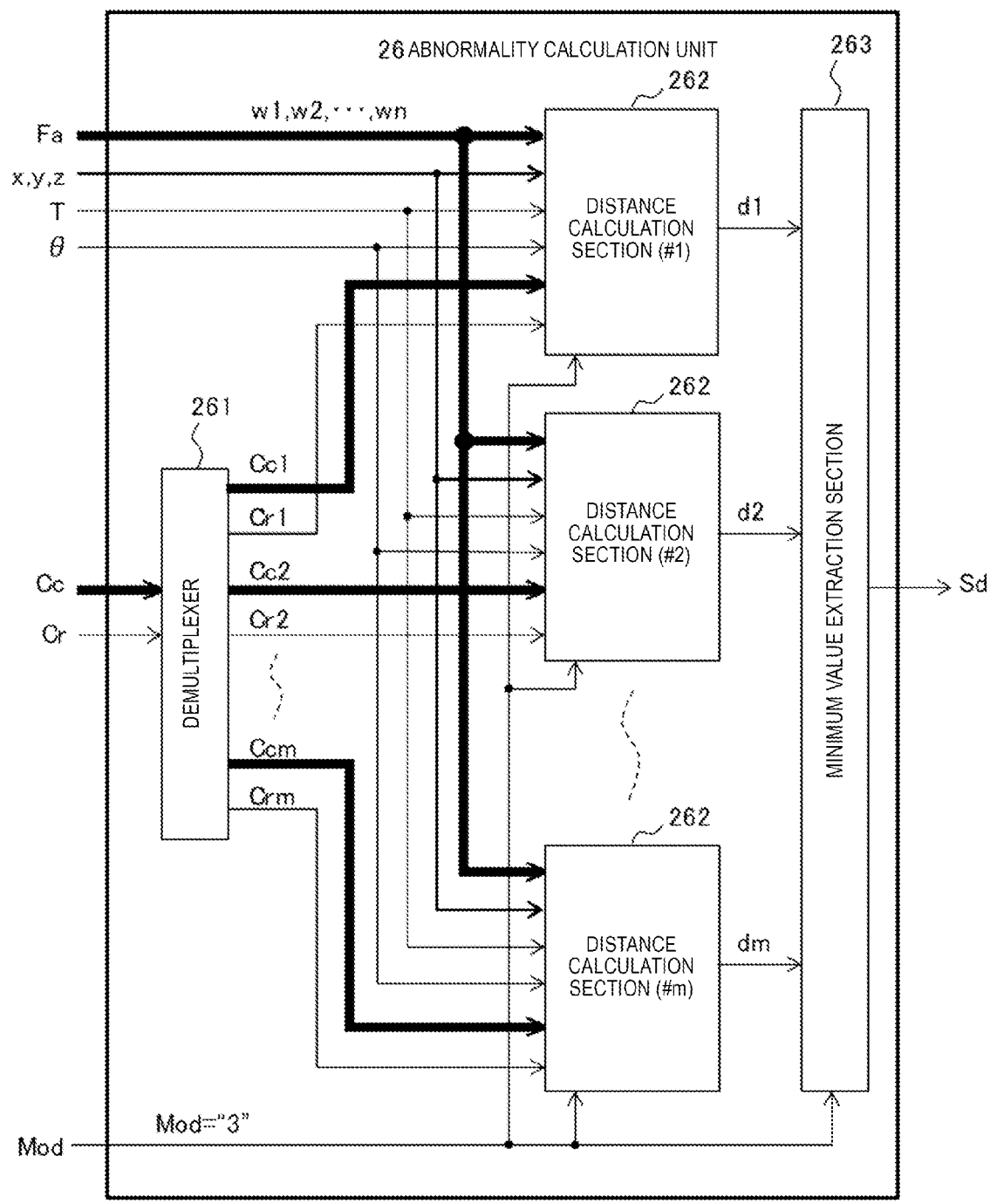

[Fig. 7]
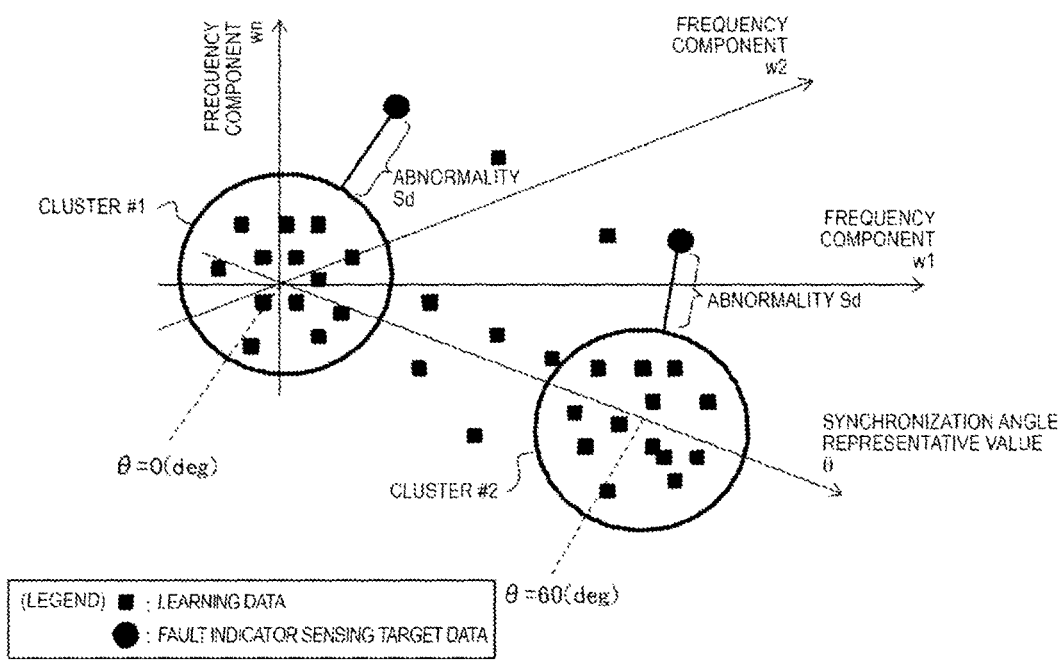

[Fig. 8]
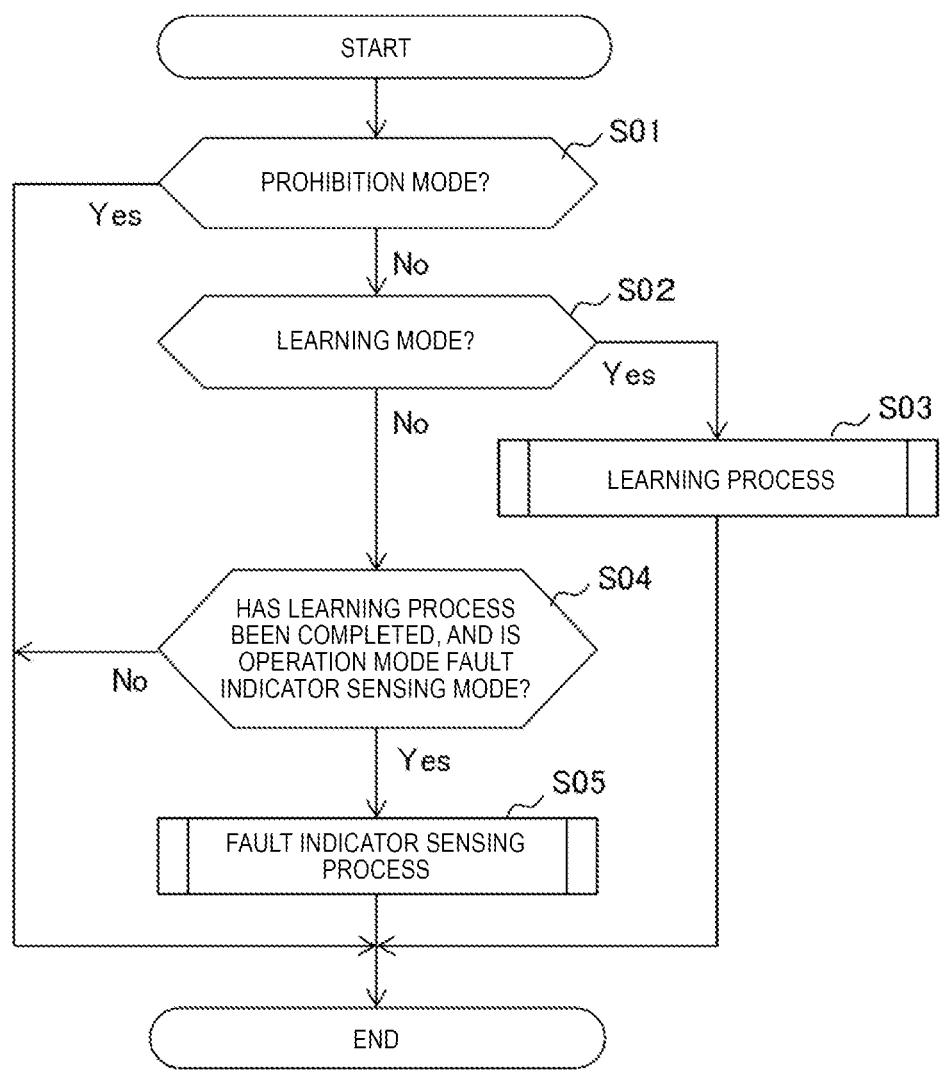

[Fig. 9]
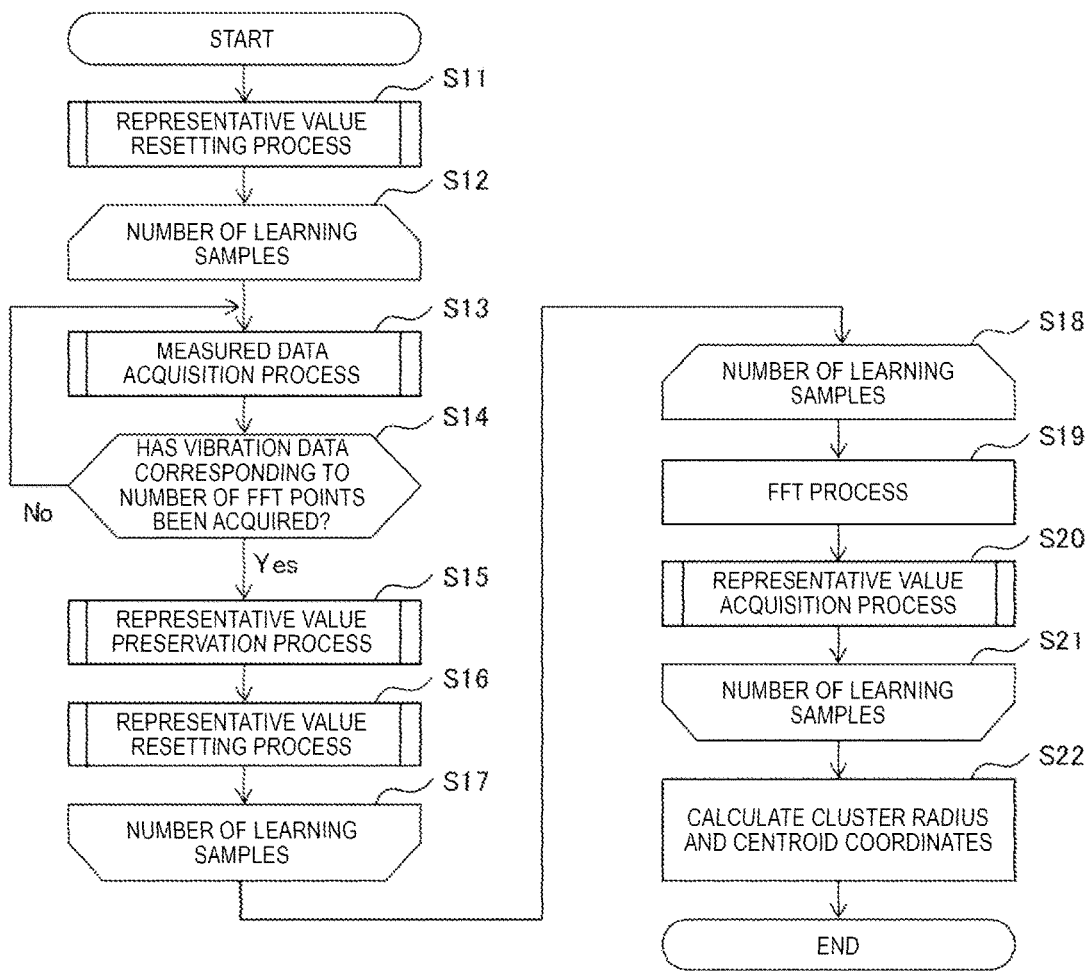

[Fig. 10]
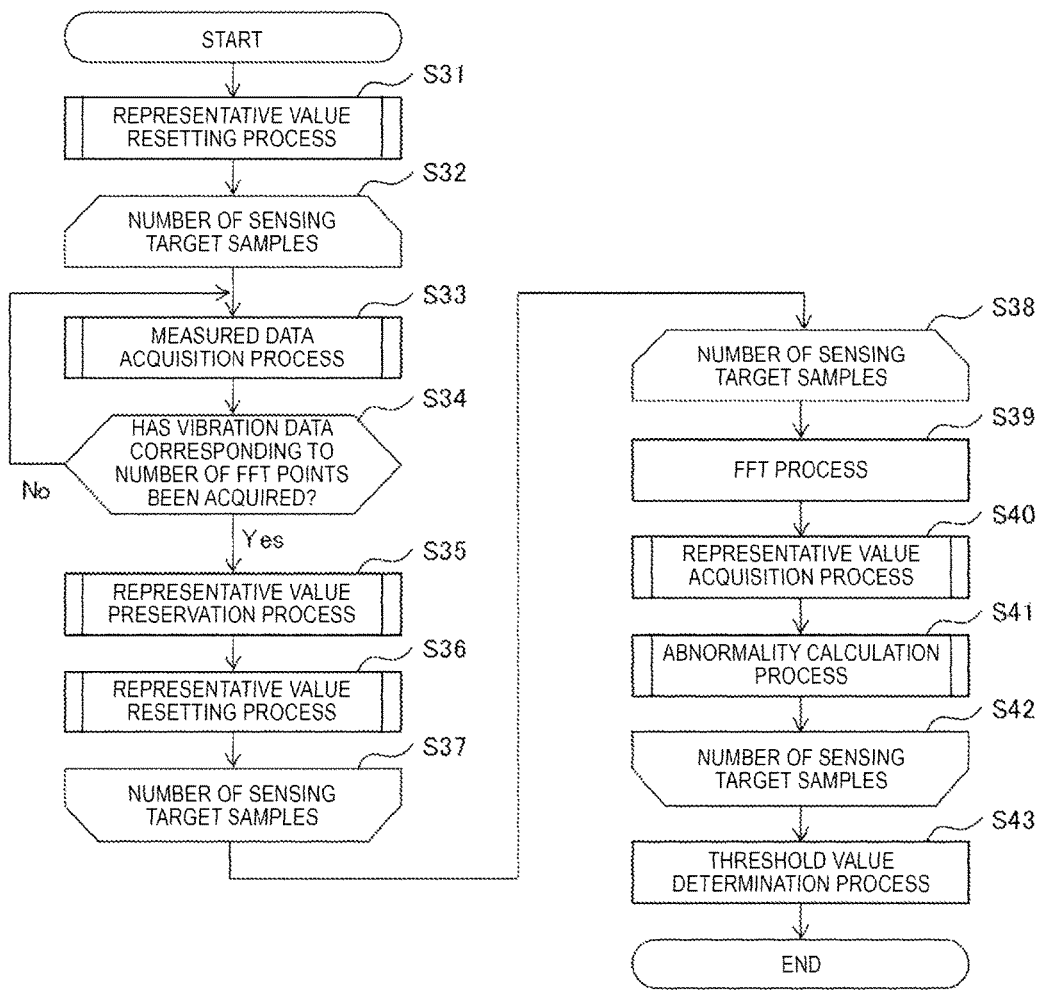

[Fig. 11]
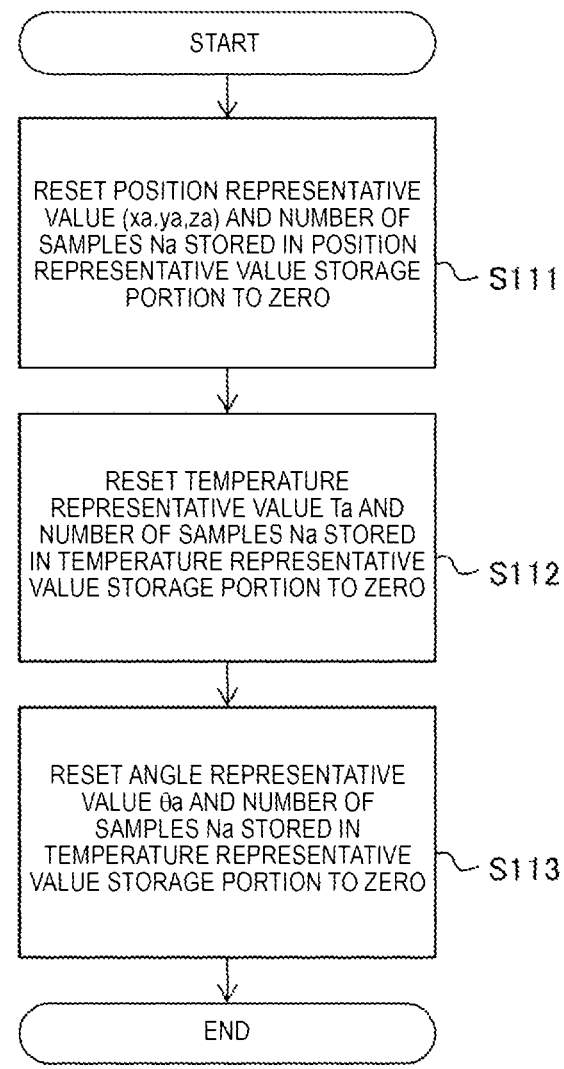

[Fig. 12]
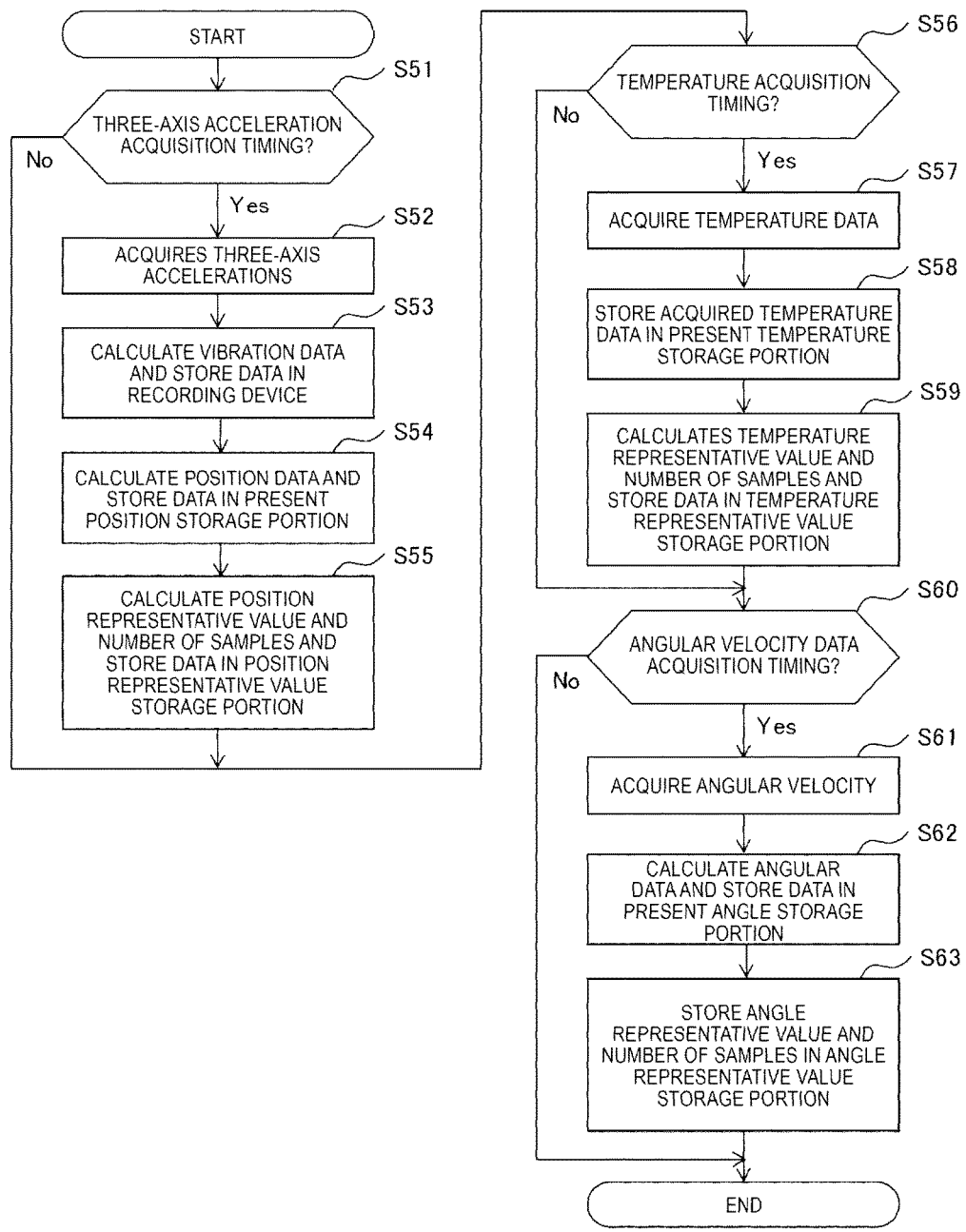

[Fig. 13]
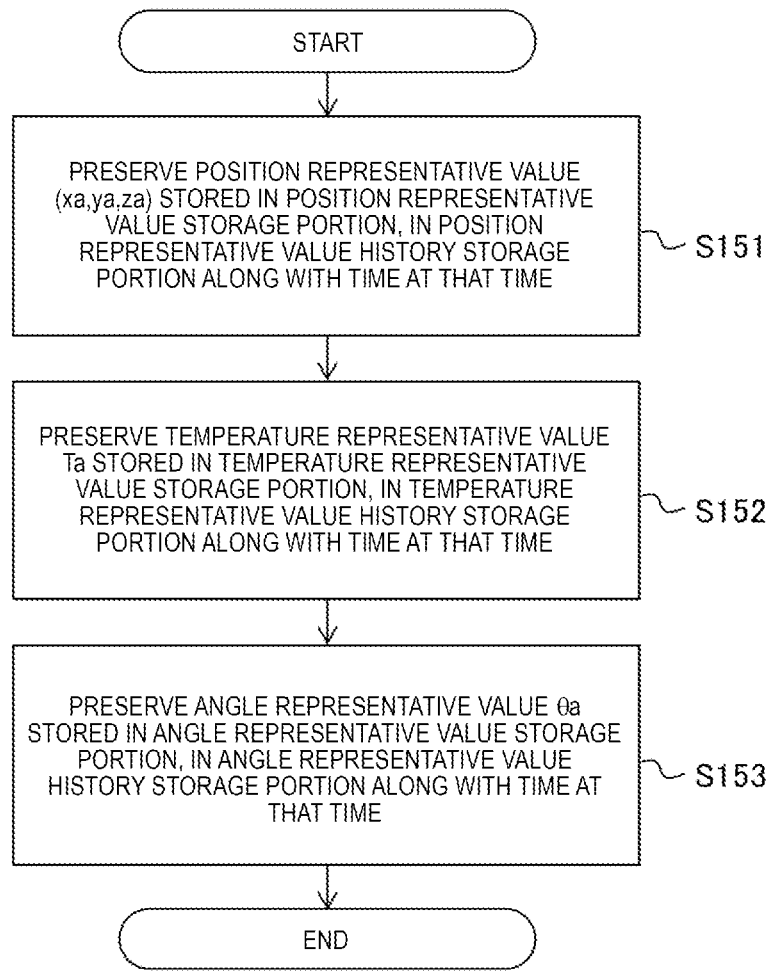

[Fig. 14]
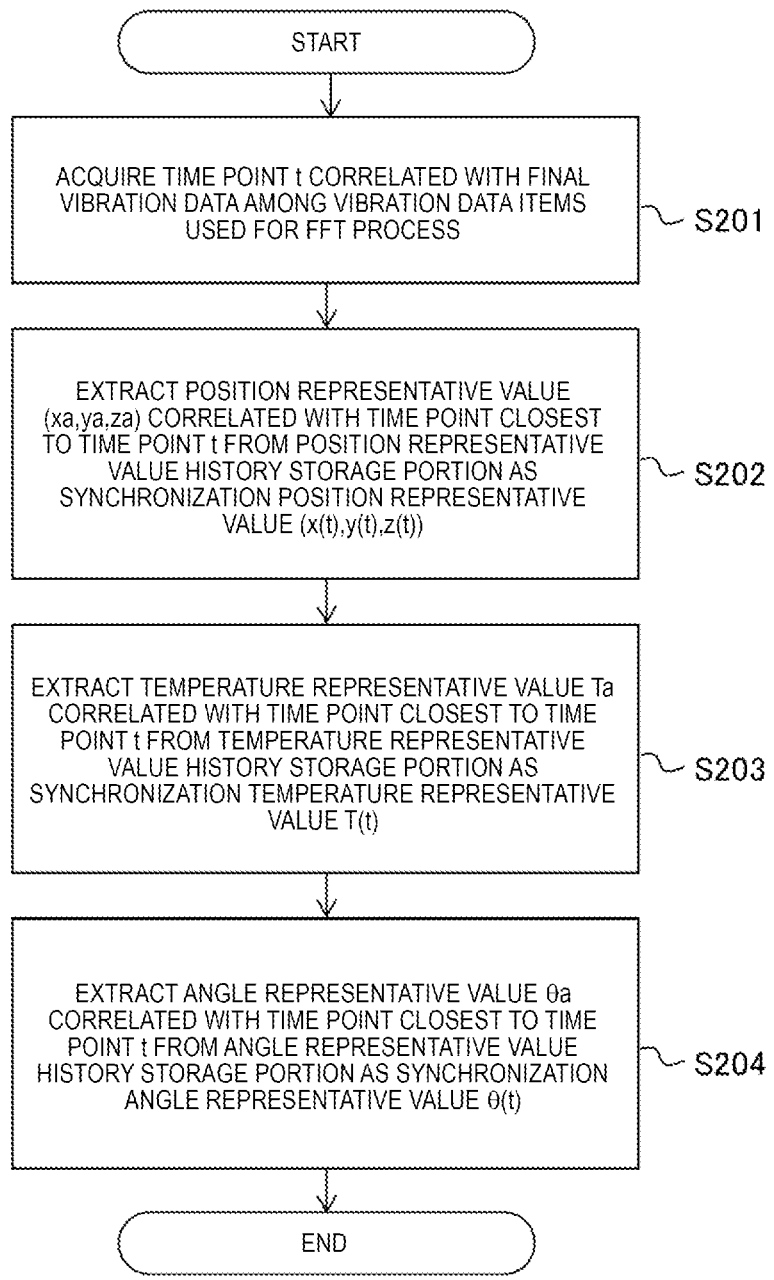

[Fig. 15]
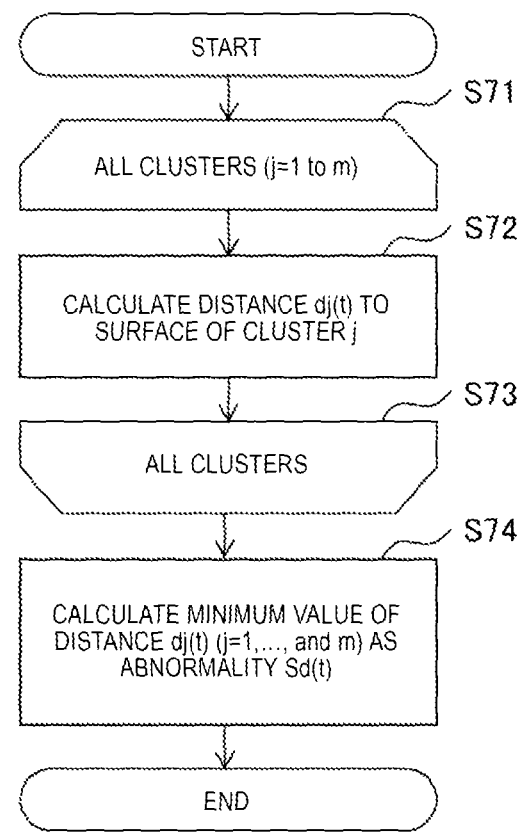

[Fig. 16]
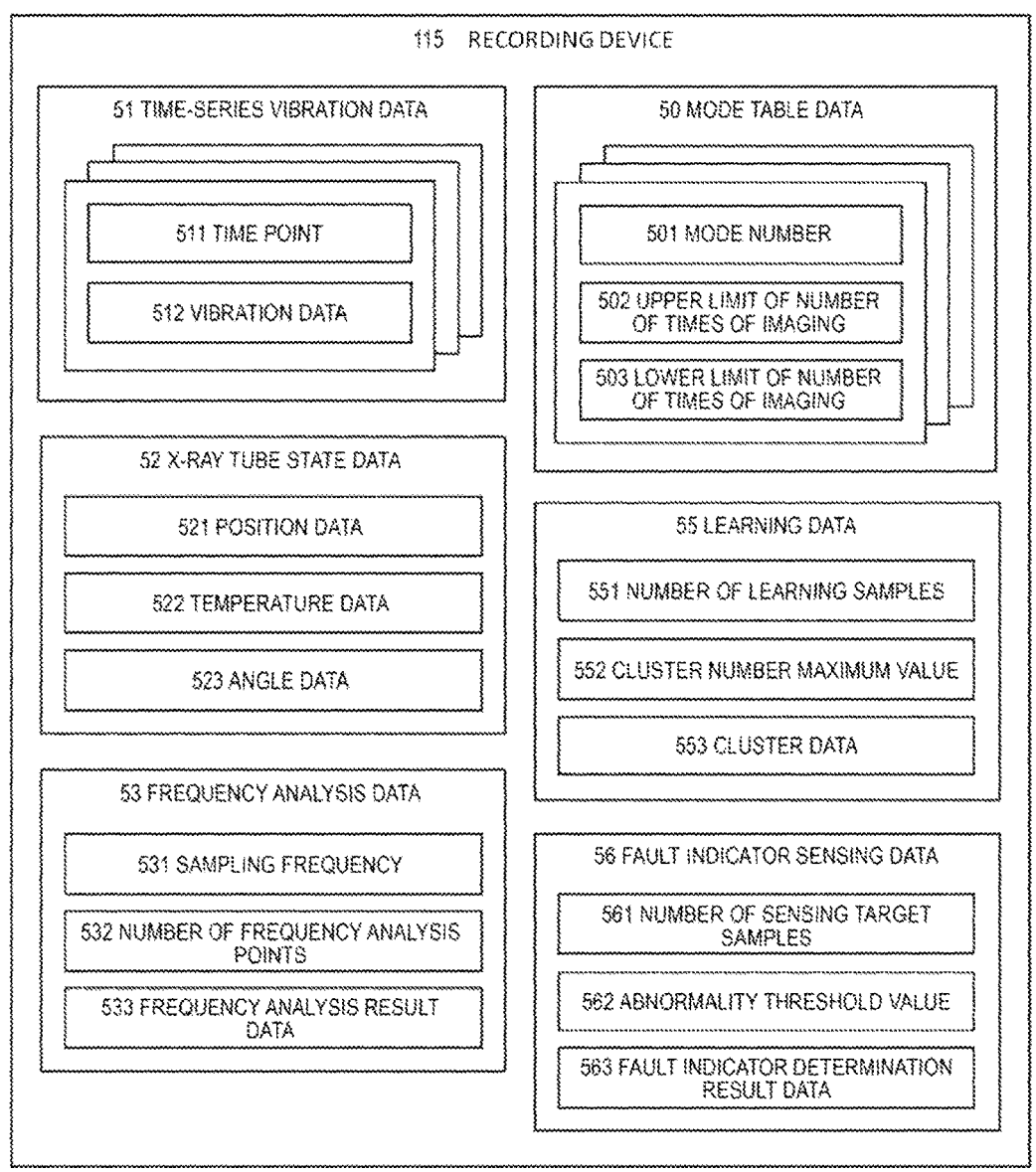

[Fig. 17]
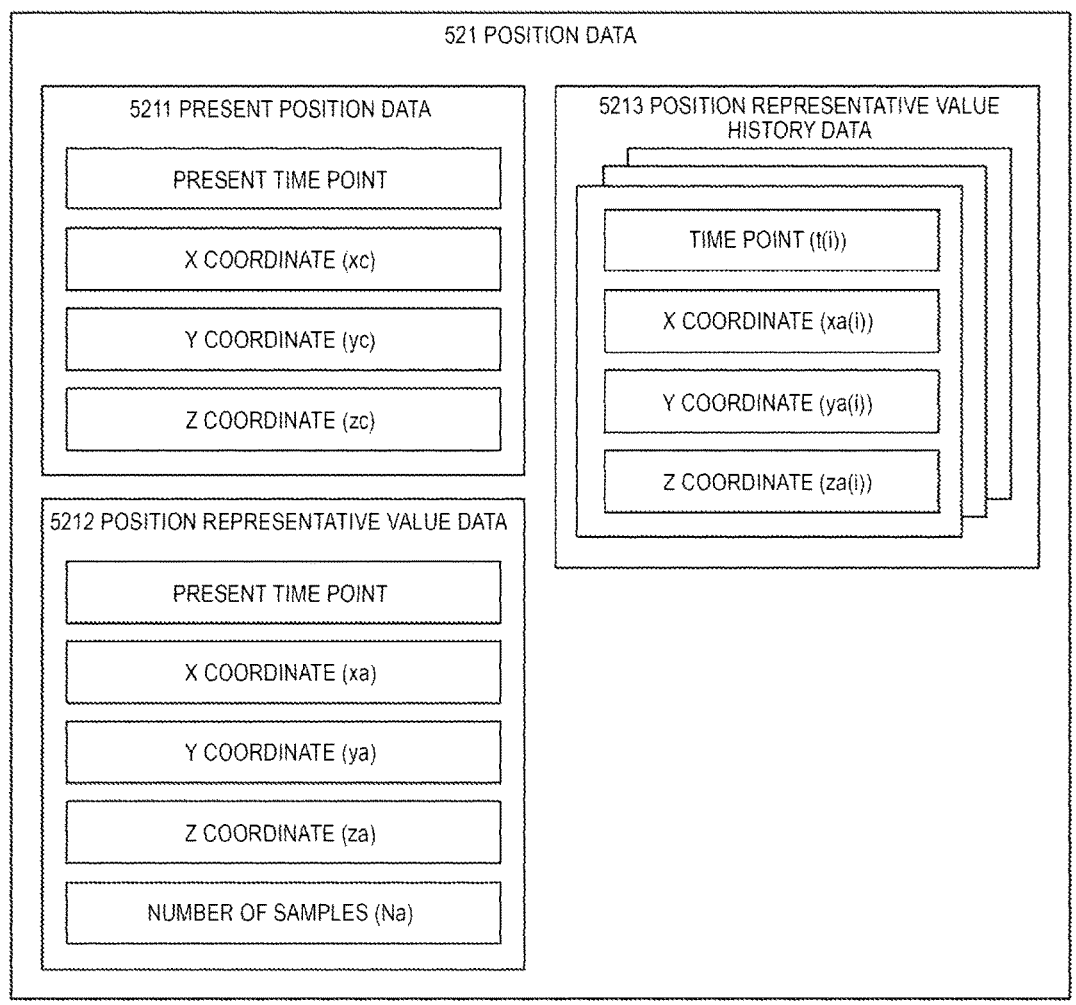

[Fig. 18]
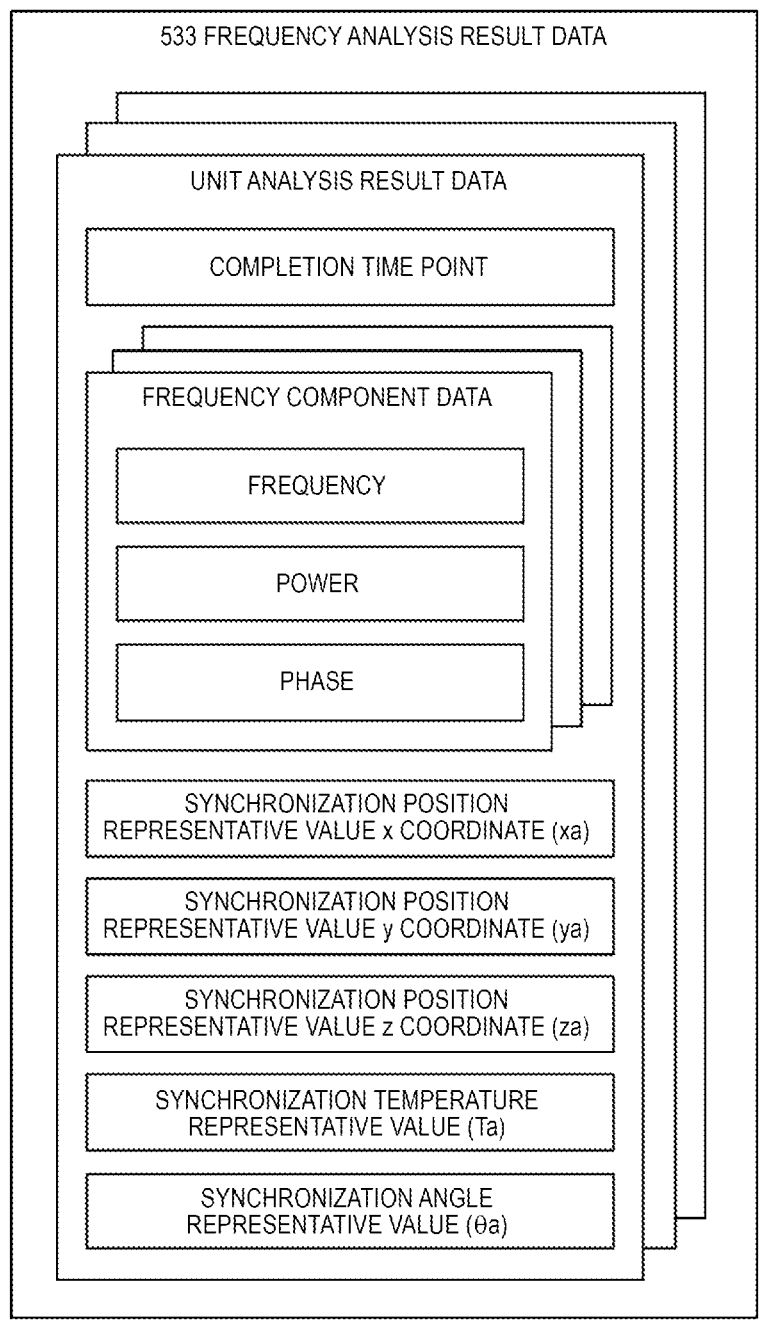

[Fig. 19]
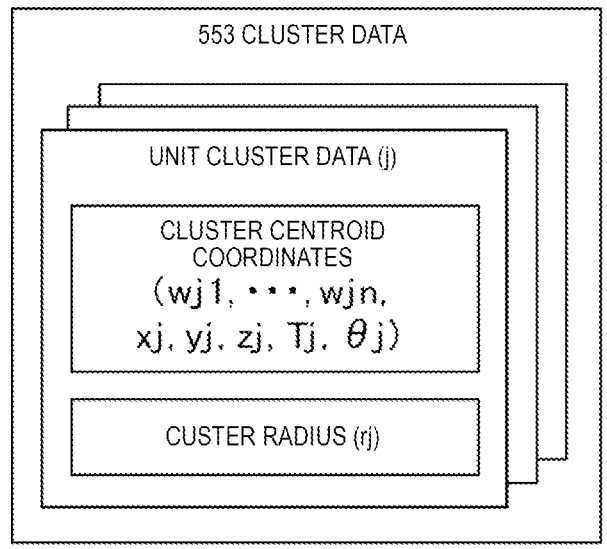
[Fig. 20]
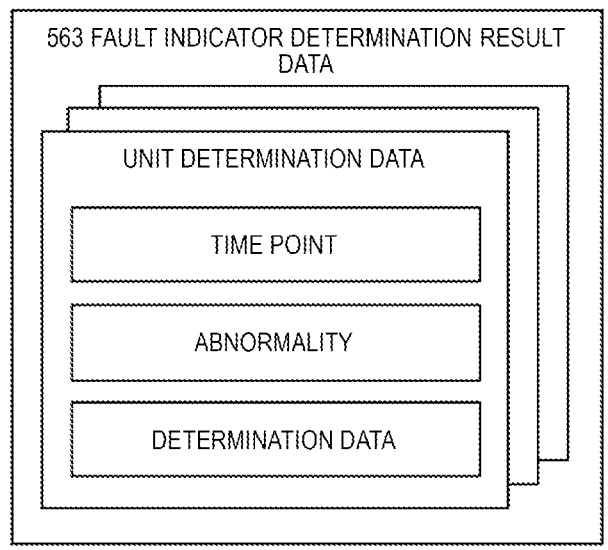

[Fig. 21]
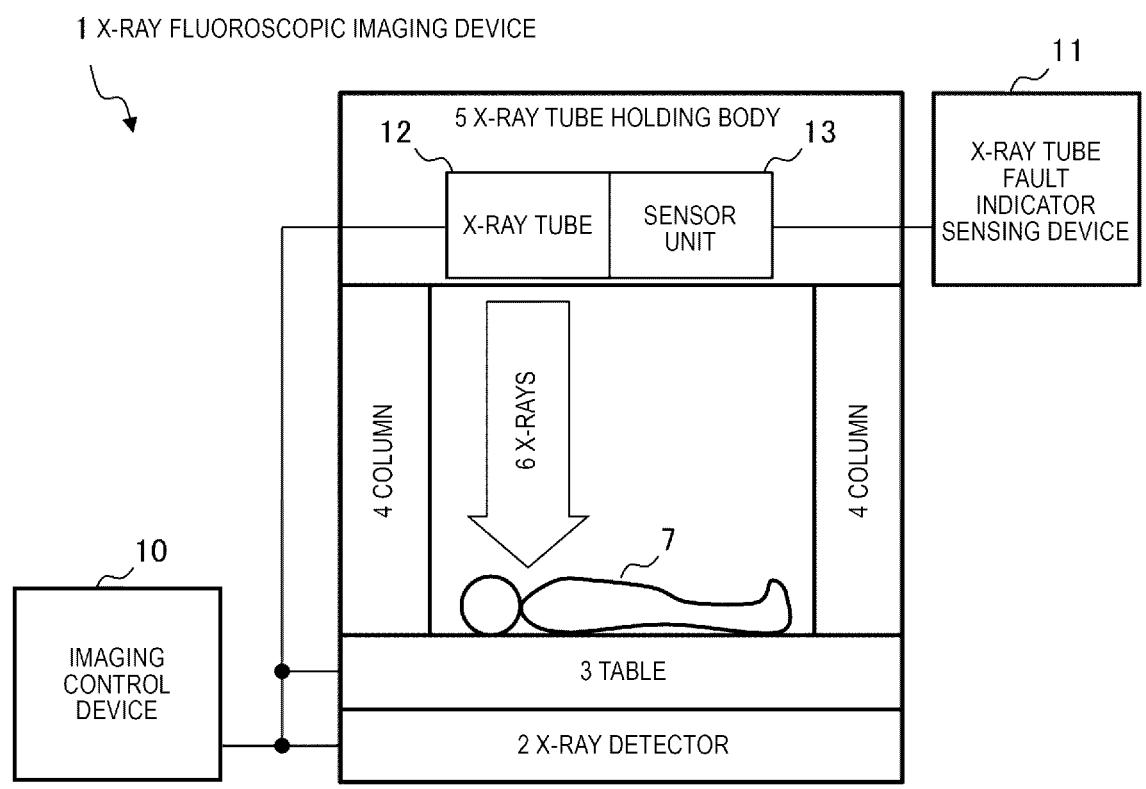

[Fig. 22]
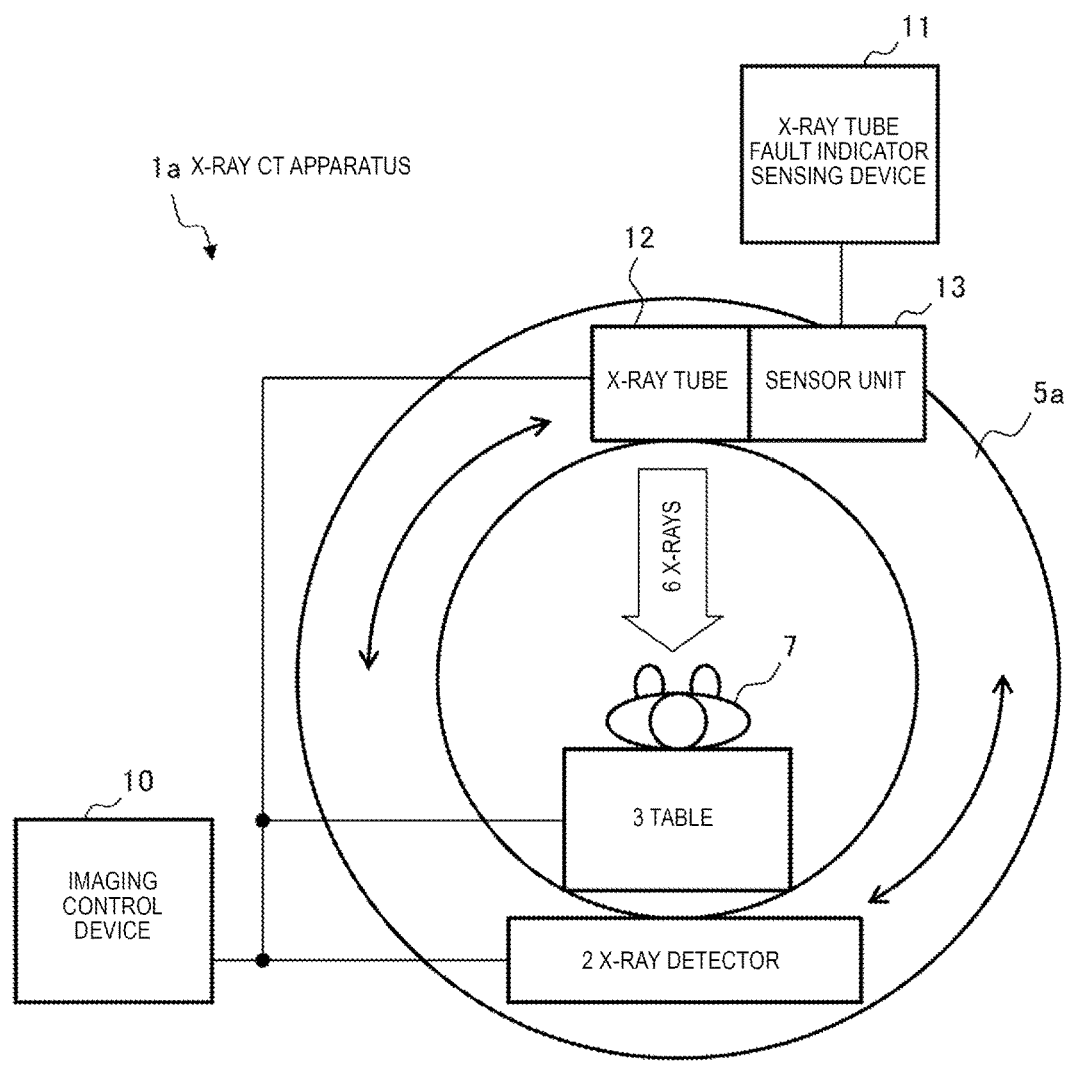

US 10,098,215 B2

X-RAY TUBE PREDICTIVE FAULT INDICATOR SENSING DEVICE, X-RAY TUBE PREDICTIVE FAULT INDICATOR SENSING METHOD, AND X-RAY IMAGING DEVICE

TECHNICAL FIELD

The present invention relates to an X-ray tube predictive fault indicator sensing device and an X-ray tube predictive fault indicator sensing method for detecting a predictive fault indicator of an X-ray tube, and an X-ray imaging device employing the X-ray tube predictive fault indicator sensing device.

BACKGROUND ART

In an X-ray imaging device such as an X-ray fluoroscopic imaging device or an X-ray computer tomography (CT) device, a type of X-ray tube which generates X-rays by applying electrons emitted from a high voltage cathode to a rotating anode is frequently used. In such an X-ray tube, a solid lubrication bearing is used to smoothly rotate the anode, but, if the solid lubrication bearing deteriorates, a fault occurs in the X-ray tube, and thus an X-ray imaging device cannot be used.

Particularly, in a medical site, it is not allowable that an X-ray imaging device cannot be used suddenly. Thus, an X-ray tube is replaced with a new product in a state in which the X-ray tube can be sufficiently used before the occurrence of a fault. This mainly causes an increase in maintenance cost for an X-ray tube. In order to reduce maintenance cost, it is necessary to use an X-ray tube as long as possible by using the X-ray tube right before a fault occurs.

It is known that, in a case where an X-ray tube is used for a long period of time, abnormal noise occurs due to deterioration or abrasion of a rotation shaft of an anode or a solid lubrication bearing. Therefore, if abnormal noise is detected, a fault of an X-ray tube can be indicated. For example, PTL 1 discloses a technique in which abnormal noise of an X-ray tube is detected with a vibration sensor, a frequency of vibration data is analyzed, a threshold value determination is performed on an amount of a specific frequency component, and thus a predictive fault indicator of the X-ray tube is detected.

PTL 2 discloses a technique in which vibration of a facility is detected with a vibration sensor, a frequency of vibration data is analyzed, a neural network is caused to learn an input frequency component of vibration data of the facility during normal times, so as to generate clusters, and vibration data of the diagnosis target facility is input to the neural network having completed the learning so that normality or abnormality of the facility is determined.

CITATION LIST

Patent Literature

PTL 1: JP-A-2011-45626
PTL 2: JP-A-2006-300896

SUMMARY OF INVENTION

Technical Problem

Generally, abnormal noise generated from an X-ray tube depends on a model of an X-ray imaging device or operation states (a position, an attitude, a temperature, and the like during operation) of the X-ray tube. This indicates that the specific frequency disclosed in PTL 1 changes depending on a model of an X-ray imaging device or operation states (a position, an attitude, a temperature, and the like during operation) of the X-ray tube. Thus, if a predictive fault indicator is to be sensed with high accuracy by using the technique disclosed in PTL 1, this requires time and effort to obtain appropriate specific frequencies or threshold values for determination according to various operation conditions of an X-ray imaging device in advance, especially, an X-ray tube, and to set such values whenever maintenance diagnosis is performed.

Therefore, it may be considered that the technique disclosed in PTL 2 is applied to an X-ray imaging device. In such an X-ray imaging device, frequency analysis is performed on vibration generated from a normal X-ray tube, a frequency analysis result causes clusters to be generated through learning using a neural network, and the clusters are used as a reference for determining a predictive fault indicator. In this case, it is possible to save time and effort to set a specific frequency disclosed in PTL 1.

However, PTL 2 does not disclose that a vibration frequency analysis result depends on operation states of the facility. This indicates that, in a case of using the technique disclosed in PTL 2, clusters used as a reference for determining a predictive fault indicator are generated on the basis of only the vibration frequency analysis result. In other words, the clusters as a reference are collectively generated regardless of operation states (a position, an attitude, a temperature, and the like during operation) of the X-ray tube, and thus it cannot be said that appropriate clusters are generated in a case of also taking into consideration the operation states (a position, an attitude, a temperature, and the like during operation) of the X-ray tube.

For example, it is considered that a frequency of vibration generated from an X-ray tube changes depending on an attitude (an angle formed by a horizontal plane of a rotation shaft of an anode) of the X-ray tube. In this case, it is not appropriate to use clusters obtained on the basis of a vibration frequency analysis result when a normal X-ray tube takes a certain attitude, to determine a predictive fault indicator of an X-ray tube taking a different attitude. If the clusters are used, a frequency of abnormal noise at a certain attitude of a deteriorating X-ray tube may possibly be included in a cluster of a frequency which is regarded to be normal at another attitude. In this case, deterioration of the X-ray tube, that is, a predictive fault indicator is not sensed. As mentioned above, if the technique disclosed in PTL 2 is just applied to an X-ray imaging device, it is difficult to sense a predictive fault indicator of an X-ray tube with high accuracy.

In light of the above-described problems of the related art, an object of the present invention is to provide an X-ray tube predictive fault indicator sensing device, an X-ray tube predictive fault indicator sensing method, and an X-ray imaging device, capable of sensing a predictive fault indicator of an X-ray tube with high accuracy.

Solution to Problem

According to the present invention, there is provided an X-ray tube predictive fault indicator sensing device including a mode setting unit that sets any one of operation modes including a prohibition mode, a learning mode, and a predictive fault indicator sensing mode; a vibration data acquisition unit that acquires vibration data regarding vibration generated from an X-ray tube, and outputs a vibration data acquisition completion notification whenever the number of acquired vibration data items reaches multiples of a predetermined number of data items used for frequency analysis performed once; a frequency analysis unit that performs frequency analysis on each of vibration data items of the predetermined number acquired by the vibration data acquisition unit; a state data acquisition unit that acquires state data indicating an operation state of the X-ray tube, and synchronizes the acquired state date with a timing at which the vibration data acquisition completion notification output from the vibration data acquisition unit is received; a learning unit that performs cluster analysis by using, as input data, a plurality of learning data items formed of frequency component data obtained through frequency analysis in the frequency analysis unit and the state data synchronized by the state data acquisition unit in a case where the learning mode is set by the mode setting unit, and generates one or more cluster data items; an abnormality calculation unit that calculates a minimum distance as an abnormality among distances to surfaces of respective clusters generated by the learning unit from a position indicated by predictive fault indicator sensing target data in a case where the predictive fault indicator sensing mode is set by the mode setting unit, the predictive fault indicator sensing target data being formed of the frequency component data obtained through frequency analysis in the frequency analysis unit and the state data synchronized by the state data acquisition unit; and a predictive fault indicator determination unit that compares the abnormality calculated by the abnormality calculation unit with a predetermined threshold value so as to determine a predictive fault indicator.

Advantageous Effects of Invention

According to the present invention, it is possible to provide an X-ray tube predictive fault indicator sensing device, an X-ray tube predictive fault indicator sensing method, and an X-ray imaging device, capable of sensing a predictive fault indicator of an X-ray tube with high accuracy.

BRIEF DESCRIPTION OF DRAWINGS

FIG. 1 is a diagram illustrating examples of configurations of an X-ray tube predictive fault indicator sensing device and an X-ray tube according to an embodiment of the present invention.

FIG. 2 is a diagram illustrating an example of a functional block configuration of the X-ray tube predictive fault indicator sensing device.

FIG. 3 is a diagram illustrating an example of a functional block configuration of a state data acquisition unit.

FIG. 4 is a diagram illustrating examples of operation modes set by a mode setting unit.

FIG. 5 is a diagram illustrating an example of a functional block configuration of a learning unit.

FIG. 6 is a diagram illustrating an example of a functional block configuration of an abnormality calculation unit.

FIG. 7 is a diagram schematically illustrating clusters and abnormality which are generated by the learning unit and are used by the abnormality calculation unit.

FIG. 8 is a diagram illustrating an example of the entire process flow in the X-ray tube predictive fault indicator sensing device according to the embodiment of the present invention.

FIG. 9 is a diagram illustrating an example of a specific process flow of a learning process.

FIG. 10 is a diagram illustrating an example of a specific process flow of a predictive fault indicator sensing process.

FIG. 11 is a diagram illustrating an example of a specific process flow of a representative value resetting process.

FIG. 12 is a diagram illustrating an example of a specific process flow of a measured data acquisition process.

FIG. 13 is a diagram illustrating an example of a specific process flow of a representative value preservation process.

FIG. 14 is a diagram illustrating an example of a specific process flow of a representative value acquisition process.

FIG. 15 is a diagram illustrating an example of a specific process flow of an abnormality calculation process.

FIG. 16 is a diagram illustrating an example of a configuration of data stored in a recording device.

FIG. 17 is a diagram illustrating an example of a specific configuration of position data included in X-ray tube state data.

FIG. 18 is a diagram illustrating an example of a specific configuration of frequency analysis result data included in frequency analysis data.

FIG. 19 is a diagram illustrating an example of a specific configuration of cluster data included in learning data.

FIG. 20 is a diagram illustrating an example of a specific configuration of predictive fault indicator determination result data included in predictive fault indicator sensing data.

FIG. 21 is a diagram schematically illustrating an example of a configuration of an X-ray fluoroscopic imaging device using the X-ray tube predictive fault indicator sensing device according to the embodiment of the present invention.

FIG. 22 is a diagram schematically illustrating an example of a configuration of an X-ray CT device using the X-ray tube predictive fault indicator sensing device according to the embodiment of the present invention.

DESCRIPTION OF EMBODIMENTS

Hereinafter, an embodiment of the present invention will be described in detail with reference to the drawings.

FIG. 1 is a diagram illustrating examples of configurations of an X-ray tube predictive fault indicator sensing device 11 and an X-ray tube 12 according to an embodiment of the present invention. As illustrated in FIG. 1, the X-ray tube 12 is configured to include an X-ray tube bulb 121 provided with a rotation anode 123 and a cathode 124 therein, a coil 122 which generates a magnetic field for rotating the rotation anode 123, and a control unit 125 which controls an AC current flowing through the coil 122, a voltage applied to the cathode 124, and the like.

Here, the rotation anode 123 is rotatably supported at an inner wall of a container of the X-ray tube bulb 121 via a solid lubrication bearing mechanism (not illustrated). The coil 122 generating a magnetic field for rotating the rotation anode 123 is disposed on an outer wall of the container portion supporting the rotation anode 123. If a high voltage is applied between the cathode 124 disposed on the inner wall of the X-ray tube bulb 121 and the rotation anode 123, electrons emitted from a filament of the cathode 124 are accelerated so as to collide with a target member 123a attached to the rotation anode 123. X-rays are generated due to the collision.

On the basis of commands from an operation console 14, the control unit 125 performs control of causing a current to flow through the coil 122 so as to rotate the rotation anode 123, and also of applying a high voltage to the cathode 124 so as to generate X-rays. Here, when a command is received from the operation console 14, the control unit 125 may generate X-rays with a predetermined time width once, and may generate in a predetermined cycle a plurality of times. The operation console 14 may be formed of push button switches and the like dedicated to the X-ray tube 12, or, alternatively, may be an operation console (input/output device) belonging to an X-ray fluoroscopic imaging device or an X-ray CT device using the X-ray tube 12.

The control unit 125 has a function of counting the number of times of imaging a subject by counting the number of times of emitting X-rays from the X-ray tube 12, and outputs a counted value thereof as number-of-times-of-imaging data Dc.

Next, a sensor unit 13 is configured to include an acceleration sensor 131, a temperature sensor 132, a gyro sensor 133, an A/D converter 134, a signal processing portion 135, and the like, and is attached to a casing of the X-ray tube 12. Here, the acceleration sensor 131, which is a so-called three-axis acceleration sensor, measures accelerations in three-dimensional directions (an x direction, a y direction, and a z direction) applied to the X-ray tube 12; the temperature sensor 132 measures the temperature of the casing of the X-ray tube 12; and the gyro sensor 133 measures an attitude angle of the X-ray tube 12. The attitude angle of the X-ray tube 12 is assumed to be an angle formed by a horizontal plane of the rotation anode 123.

The A/D converter 134 converts an analog signal measured by each of the acceleration sensor 131, the temperature sensor 132, and the gyro sensor 133 into digital data.

The signal processing portion 135 removes a frequency component which is not necessary in predictive fault indicator sensing (hereinafter, simply referred to as sensing) for the X-ray tube 12 from each digital data item obtained as a result of A/D conversion. The signal processing portion 135 converts three-dimensional acceleration data obtained from the acceleration sensor 131 into vibration data generated from the X-ray tube 12, and outputs the vibration data as vibration data Dv. The signal processing portion 135 performs two-step integration on the three-dimensional acceleration data in each direction so as to calculate and output three-dimensional position data Dp indicating a position of the X-ray tube 12. The signal processing portion 135 processes a measurement value of the temperature obtained from the temperature sensor 132, so as to output temperature data Dt, and processes a measurement value of an attitude angle obtained from the gyro sensor 133 so as to output angle data Da.

In the sensor unit 13, the A/D converter 134 and the signal processing portion 135 may be reversed in a processing order thereof. As a sensor sensing vibration generated from the X-ray tube 12, a microphone sensing voices may be used instead of the acceleration sensor 131.

As illustrated in FIG. 1, the X-ray tube predictive fault indicator sensing device 11 is configured to include a display device 111, an alarm device 112, a central processing unit 113, an operation input device 114, a recording device 115, a storage device 116, an I/O port 117, and the like, and has a configuration of a general computer such as a so-called PC.

Here, the I/O port 117 incorporates the vibration data Dv, the position data Dp, the temperature data Dt, and the angle data Da output from the sensor unit 13, and the number-of-times-of-imaging data Dc output from the X-ray tube 12, according to an output timing of each data item, and writes each data item in the recording device 115. The recording device 115 is a storage device which records data required in an X-ray tube predictive fault indicator sensing process, and, in the present embodiment, the recording device 115 is differentiated from the storage device 116 which stores programs or temporary data.

The central processing unit 113 executes a program stored in advance in the storage device 116 so as to realize various functions of the X-ray tube predictive fault indicator sensing device 11. The functions will be described in detail with reference to FIG. 2 and the subsequent drawings.

The display device 111 performs display for requesting an operator's permission or prohibition of a predictive fault indicator sensing process or a learning process for the X-ray tube 12 according to a program executed by the central processing unit 113. The operation input device 114 is used for the operator to input instruction data for permission or prohibition of a predictive fault indicator sensing process or a learning process for the X-ray tube 12, and the alarm device 112 is used to issue an alarm, for example, in a case where a predictive fault indicator is detected as a result of a predictive fault indicator sensing process for the X-ray tube 12.

FIG. 2 is a diagram illustrating an example of a functional block configuration of the X-ray tube predictive fault indicator sensing device 11. As illustrated in FIG. 2, the X-ray tube predictive fault indicator sensing device 11 is configured to include a vibration data acquisition unit 20, a frequency analysis unit 21, a state data acquisition unit 22, a prohibition flag setting unit 23, a mode setting unit 24, a learning unit 25, an abnormality calculation unit 26, a predictive fault indicator determination unit 27, and the like. The functions of the functional block are realized by the central processing unit 113 of the X-ray tube predictive fault indicator sensing device 11 executing a program stored in advance in the storage device 116.

FIG. 2 also illustrates examples of partial functional block configurations of the X-ray tube 12 and the sensor unit 13 for reference.

The vibration data acquisition unit 20 acquires the vibration data Dv which is output from a vibration data output portion 1351 of the sensor unit 13 in a predetermined cycle, and stores the acquired vibration data Dv in the recording device 115 (refer to FIG. 1) along with the time at that time. The vibration data output portion 1351 outputs a vibration data acquisition completion notification Ve indicating that the vibration data Dv for frequency analysis has been acquired whenever the number of acquired vibration data items Dv exceeds multiples of the number thereof (which corresponds to, for example, the number of FFT points, and will be hereinafter referred to as the number of frequency analysis target data items) used for frequency analysis performed once.

The frequency analysis unit 21 acquires separate vibration data items corresponding to the number of frequency analysis target data items on the basis of the vibration data which is acquired by the vibration data acquisition unit 20 and is stored in the recording device 115, and performs frequency analysis such as fast Fourier transform (FFT) on the acquired vibration data so as to output a frequency analysis result thereof as a frequency analysis result Fa.

The state data acquisition unit 22 acquires the position data Dp, the temperature data Dt, and the angle data Da which are output from a position data output portion 1352, a temperature data output portion 1353, and an angle data output portion 1354 of the sensor unit 13 in different cycles. The position data Dp, the temperature data Dt, and the angle data Da which are acquired in the different cycles are synchronized with a timing at which the vibration data acquisition completion notification Ve output from the frequency analysis unit 21 is received.

Specifically, the state data acquisition unit 22 calculates, for example, an average value for each of the position data Dp, the temperature data Dt, and the angle data Da which are obtained while the vibration data acquisition unit 20 acquires the vibration data Dv corresponding to frequency analysis performed once, and outputs respective average values thereof as a synchronization position representative value xyz, a synchronization temperature representative value T, and a synchronization angle representative value θ.

More specific configuration and functions of the state data acquisition unit 22 will be described later with reference to FIG. 3.

The prohibition flag setting unit 23 sets a value of a prohibition flag Fi according to data which is input by the operator via the operation input device 114 (refer to FIG. 1). Here, it is assumed that both of a predictive fault indicator sensing process and a learning process in the X-ray tube predictive fault indicator sensing device 11 are prohibited if a value of the prohibition flag Fi is "1", and are permitted if a value of the prohibition flag Fi is "0".

The mode setting unit 24 sets an operation mode of the X-ray tube predictive fault indicator sensing device 11 on the basis of number-of-times-of-imaging data Dc counted by a number-of-times-of-imaging counting portion 1251 of the control unit 125 of the X-ray tube 12, and the prohibition flag Fi set by the prohibition flag setting unit 23. Here, it is assumed that the operation mode includes three modes such as a prohibition mode, a learning mode, and a predictive fault indicator sensing mode. In other words, the mode setting unit 24 sets a mode number Mod ("1", "2", or "3") according to each of the prohibition mode, the learning mode, and the predictive fault indicator sensing mode, and outputs the mode number.

A relationship between input data (the number-of-times-of-imaging data Dc and the prohibition flag Fi) of the mode setting unit 24 and a mode number Mod set by the mode setting unit 24 will be described later with reference to FIG. 4.

When the learning mode (Mod="2") is set by the mode setting unit 24, the learning unit 25 performs cluster analysis by using the frequency analysis result Fa output from the frequency analysis unit 21, and the synchronization position representative value xyz, the synchronization temperature representative value T, and the synchronization angle representative value θ output from the state data acquisition unit 22 as input data, so as to generate one or more clusters. Centroid coordinates Cc and a radius Cr are calculated for each of the generated clusters.

More specific configuration and functions of the learning unit 25 will be described later with reference to FIG. 5.

When the predictive fault indicator sensing mode (Mod="3") is set by the mode setting unit 24, the abnormality calculation unit 26 calculates distances between coordinates indicated by the frequency analysis result Fa analyzed by the frequency analysis unit 21, and the synchronization position representative value xyz, the synchronization temperature representative value T, and the synchronization angle representative value θ output from the state data acquisition unit 22, and centroid coordinates Ccj of each cluster j, with respect to the vibration data Dv obtained from the X-ray tube 12 which is a predictive fault indicator sensing target. The abnormality calculation unit 26 calculates values dj obtained by subtracting a radius Crj of each cluster j from the calculated distances, obtains the minimum value among the calculated values dj, and outputs the minimum value as an abnormality Sd.

More specific configuration and functions of the abnormality calculation unit 26 will be described later with reference to FIG. 6.

When the predictive fault indicator sensing mode (Mod="3") is set by the mode setting unit 24, the predictive fault indicator determination unit 27 compares the abnormality Sd calculated by the abnormality calculation unit 26 with a predetermined threshold value so as to determine the presence or absence of a predictive fault indicator for the X-ray tube 12 which is a predictive fault indicator sensing target, and outputs a determination result Sp thereof.

For example, "0" may be used as the predetermined threshold value. In this case, if the abnormality Sd is equal to or less than "0" ("0" or a negative value), it is determined that a predictive fault indicator is not sensed, and if the abnormality Sd is more than "0" (a positive value), it is determined that a predictive fault indicator is sensed.

In other words, in a case where coordinates indicated by the frequency analysis result Fa, the synchronization position representative value xyz, the synchronization temperature representative value T, and the synchronization angle representative value θ for the vibration data Dv obtained from the X-ray tube 12 which is a predictive fault indicator sensing target are included in any one of the clusters (the centroid coordinates Cc and the radius Cr thereof) generated by the learning unit 25, it is determined that a predictive fault indicator is not sensed, and in a case where the coordinates are not included in any cluster, it is determined that a predictive fault indicator is sensed.

FIG. 3 is a diagram illustrating an example of a functional block configuration of the state data acquisition unit 22. As illustrated in FIG. 3, the state data acquisition unit 22 is configured to include a position representative value acquisition section 221, a temperature representative value acquisition section 222, and an angle representative value acquisition section 223. The position representative value acquisition section 221, the temperature representative value acquisition section 222, and the angle representative value acquisition section 223 respectively calculate the synchronization position representative value xyz, the synchronization temperature representative value T, and the synchronization angle representative value θ at timings at which the vibration data acquisition completion notification Ve is received from the vibration data acquisition unit 20, record the values in the recording device 115 (refer to FIG. 1), and output the values as necessary.

In the state data acquisition unit 22, the position representative value acquisition section 221 is configured to include a present position storage portion 2211, a position representative value calculation portion 2212, a position representative value storage portion 2213, and a position representative value history storage portion 2214. Similarly, the temperature representative value acquisition section 222 is configured to include a present temperature storage portion 2221, a temperature representative value calculation portion 2222, a temperature representative value storage portion 2223, and a temperature representative value history storage portion 2224. The angle representative value acquisition section 223 is configured to include a present angle storage portion 2231, an angle representative value calculation portion 2232, an angle representative value storage portion 2233, and an angle representative value history storage portion 2234.

Here, a configuration and functions of the position representative value acquisition section 221 will be described in detail. In a case where the mode number Mod is "2" or "3" (the learning mode or the predictive fault indicator sensing mode), the present position storage portion 2211 acquires and stores three-dimensional position data Dp (xc, yc, zc) which is output from the sensor unit 13 in a predetermined cycle (for example, 10 msec).

When the position data Dp (xc, yc, zc) is acquired by the present position storage portion 2211, the position representative value calculation portion 2212 calculates new position representative values (xa', ya', za') and a new number of samples Na' according to the following Equations (1) and (2) by using the position data Dp (xc, yc, zc) acquired at that time, position representative values (xa, ya, za) stored in the position representative value storage portion 2213 and the number of samples Na at that time.

$$xa' = \{xa \cdot Na + xc\}/(Na+1)$$

$$ya' = \{ya \cdot Na + yc\}/(Na+1)$$

$$za' = \{za \cdot Na + zc\}/(Na+1) \quad (1)$$

$$Na' = Na + 1 \quad (2)$$

In Equations (1) and (2), the number of samples Na is the number of position data Dp (xc, yc, zc) used to calculate position representative values before this point. Here, initial values of the position representative values (xa, ya, za) and the number of samples Na are all zeros, and are reset to zeros whenever the number of vibration data items Dv acquired by the vibration data acquisition unit 20 exceeds the number of frequency analysis target data items. In other words, the initial values thereof are reset to zeros whenever the vibration data acquisition completion notification Ve is received from the vibration data acquisition unit 20.

When the vibration data acquisition completion notification Ve is received from the vibration data acquisition unit 20, the position representative value history storage portion 2214 accumulates data obtained by adding a time point t at that time to the position representative values (xa, ya, za) stored in the position representative value storage portion 2213 at that point, as position representative value history data (t(i), xa(i), ya(i), za(i)). Here, i is a number added in the order of time for the purpose of identifying position representative value history data.

The position representative value history storage portion 2214 extracts position representative value history data (t(i), xa(i), ya(i), za(i)) closest to the designated time point t in response to a request from the learning unit 25 or the abnormality calculation unit 26, and outputs the data as synchronization position representative values xyz (x, y, z).

Similarly, the temperature representative value acquisition section 222 outputs the synchronization temperature representative value T from the temperature representative value history storage portion 2224, and the angle representative value acquisition section 223 outputs the synchronization angle representative value θ from the angle representative value history storage portion 2234.

FIG. 4 is a diagram illustrating examples of operation modes set by the mode setting unit 24. As illustrated in FIG. 4, the prohibition flag Fi and the number-of-times-of-imaging data Dc are input to the mode setting unit 24, and any one of operation modes including the prohibition mode, the learning mode, and the predictive fault indicator sensing mode is set according to input values thereof. The mode setting unit 24 outputs the mode number Mod such as "1", "2", or "3" according to each operation mode.

As illustrated in FIG. 4, in a case where the prohibition flag Fi is "1", the prohibition mode is set regardless of a value of the number-of-times-of-imaging data Dc. In the prohibition mode, neither the learning process nor the predictive fault indicator sensing process is performed. In a case where the prohibition flag Fi is "0", and the number-of-times-of-imaging data Dc is 9 or less, that is, a first upper limit value or less, the prohibition mode is set. In a case where the prohibition flag Fi is "0", and the number-of-times-of-imaging data Dc is 10 or more and 19 or less, that is, a second upper limit value or less, the learning mode is set, and in a case where the number-of-times-of-imaging data Dc is 20 or more and 9,999,999 or less, the predictive fault indicator sensing mode is set.

A lower limit value and an upper limit value of the number-of-times-of-imaging data Dc determining each operation mode are not limited to the values illustrated in FIG. 4. The number-of-times-of-imaging data Dc output from the number-of-times-of-imaging counting portion 1251 of the X-ray tube 12 may be reset to zero when a predetermined time elapses, for example, once a day or a week, or when the number of times of imaging exceeds a predetermined number of times (for example, 100).

As mentioned above, in the prohibition mode set on the basis of the number-of-times-of-imaging data Dc, the learning process and the predictive fault indicator sensing process are automatically prohibited from being performed on vibration data which is different from at normal times, during an initial operation or a running-in operation, in an X-ray imaging device or an X-ray CT device using the X-ray tube predictive fault indicator sensing device 11. Consequently, it is possible to reduce a work burden on a worker and also to prevent learning errors or sensing errors during an initial operation or a running-in operation.

FIG. 5 is a diagram illustrating an example of a functional block configuration of the learning unit 25. As illustrated in FIG. 5, the learning unit 25 is configured to include a demultiplexer 251, a cluster data generation section 252, and a multiplexer 253.

Here, the demultiplexer 251 to which the frequency analysis result Fa is input decomposes the input frequency analysis result Fa into frequency components w1, w2, . . . , and wn. The frequency components w1, w2, . . . , and wn, and the synchronization position representative values xyz (x, y, z), the synchronization temperature representative value T, and the synchronization angle representative value θ output from the state data acquisition unit 22 are input to the cluster data generation section 252.

The cluster data generation section 252 regards data such as the frequency components w1, w2, . . . , and wn, the synchronization position representative values xyz (x, y, z), the synchronization temperature representative value T, and the synchronization angle representative value θ which are input, as (n+5)-dimensional vector components, and performs a cluster generation process on the (n+5)-dimensional vectors. In the cluster generation process, at least one cluster (m clusters: m≥1) is generated, centroid coordinates Cc1, Cc2, . . . , and Ccm and radii Cr1, Cr2, . . . , and Crm are calculated for the respective clusters. In the cluster generation process, for example, well-known k-means clustering may be used.

The multiplexer 253 gathers the centroid coordinates Cc1, Cc2, . . . , and Ccm, and the radii Cr1, Cr2, . . . , and Crm calculated by the cluster data generation section 252 together, so as to output cluster centroid coordinates Cc and a cluster radius Cr.

The mode number Mod is input to the cluster data generation section 252 as a signal for permitting an operation thereof. Here, when the mode number Mod="2" is input, that is, when an operation mode is the learning mode, the cluster generation process is performed in the cluster data generation section 252.

FIG. 6 is a diagram illustrating an example of a functional block configuration of the abnormality calculation unit 26. As illustrated in FIG. 6, the abnormality calculation unit 26 is configured to include a demultiplexer 261, m distance calculation sections 262, and a minimum value extraction section 263.

Here, the demultiplexer 261 to which the cluster centroid coordinates Cc and the cluster radius Cr are input decomposes the input cluster centroid coordinates Cc and radius Cr into m cluster centroid coordinates Cc1, Cc2, ..., and Ccm, and m radii Cr1, Cr2, ..., and Crm. The centroid coordinates Ccj and the radius Crj of the j-th cluster are input to the distance calculation section 262 (#j), and also the frequency analysis result Fa, the synchronization position representative values xyz (x, y, z), the synchronization temperature representative value T, and the synchronization angle representative value θ are input thereto. The frequency analysis result Fa mentioned here indicates the frequency components w1, w2, ..., and wn obtained as a result of decomposition in a demultiplexer (not illustrated).

With respect to the (n+5)-dimensional vectors having the frequency components w1, w2, ..., and wn, the synchronization position representative values xyz (x, y, z), the synchronization temperature representative value T, and the synchronization angle representative value θ as components, the distance calculation section 262 (#j) calculates a distance between a position indicated by the vectors and a position indicated by the centroid coordinates Ccj of the j-th cluster, and outputs a distance obtained by subtracting the radius Crj from the distance, as a distance dj to a surface of the j-th cluster.

In other words, the distance calculation section 262 (#j) calculates the distance dj to the surface of the j-th cluster according to the following equations.

$$dj(t) = \sqrt{djw(t) + djxyz(t) + djT(t) + djθ(t)} - rj \quad (3)$$

$$djw(t) = \sum_{k=1}^{n} (wk(t) - wjk)^2 \quad (4)$$

$$djxyz(t) = (x(t)-xj)^2 + (y(t)-yj)^2 + (z(t)-zj)^2 \quad (5)$$

$$djT(t) = (T(t)-Tj)^2 \quad (6)$$

$$djθ(t) = (θ(t)-θj)^2 \quad (7)$$

In addition, coordinates expressed as (wj1, wj2, ..., wjn, xj, yj, zj, Tj, θj) by using the parameter symbols used in the above Equations (3) to (7) correspond to the centroid coordinates Ccj of the j-th cluster. In addition, rj shown in Equation (3) corresponds to the radius Crj of the j-th cluster described in FIG. 5.

Similarly, a vector Vt expressed as (w1 (t), w2 (t), ..., wn(t), x(t), y(t), z(t), T(t), θ(t)) by using the variable symbols used in the above Equations (3) to (7) indicates input data for a predictive fault indicator sensing target which is input to each of the m distance calculation sections 262 (#j) (refer to FIG. 6) in synchronization with the time point t. In other words, the variable symbol wk(t) corresponds to the frequency components w1, w2, ..., and wn as the frequency analysis result Fa described in FIG. 6, and the variable symbols x(t), y(t) andz(t), the variable symbol T(t), and the variable symbol θ(t) respectively correspond to the synchronization position representative values xyz (x, y, z), the synchronization temperature representative value T, and the synchronization angle representative value θ described in FIG. 6. Therefore, dj(t) shown in Equation (3) indicates the distance dj to the surface of the j-th cluster from a coordinate position indicated by the input vector Vt synchronized with the time point t.

Next, the minimum value extraction section 263, to which distances d1, d2, ..., and dm which are respectively output from the m distance calculation sections 262 are input, extracts the minimum value from among the input distances d1, d2, ..., and dm, and outputs the extracted minimum value as the abnormality Sd. However, in a case where the extracted minimum value is a negative value, the minimum value extraction section 263 outputs, for example, the abnormality Sd=0. In this case, if a determination threshold value is "0", it is determined that there is no abnormality, that is, a predictive fault indicator is not sensed.

The mode number Mod is input to the cluster data generation section 252 (refer to FIG. 5) as a signal for permitting an operation thereof. Here, when the mode number Mod="3" is input, that is, when an operation mode is the predictive fault indicator sensing mode, the cluster generation process is performed in the cluster data generation section 252.

FIG. 7 is a diagram schematically illustrating examples of clusters and abnormality which are generated by the learning unit 25 and are used by the abnormality calculation unit 26. As described above, a cluster in the present embodiment is generated in the (n+5)-dimensional space, it is difficult to display the space on a two-dimensional plane, but FIG. 7 schematically illustrates only coordinate axes of the frequency components w1, w2 and wn, and a coordinate axis of the synchronization angle representative value θ. In FIG. 7, a black square mark indicates data (learning data) which is input during the learning mode, and a black circle mark indicates data (predictive fault indicator sensing target data) which is input during the predictive fault indicator sensing mode.

As illustrated in FIG. 7, in the learning mode, the learning unit 25 generates a cluster #1 and a cluster #2 represented as multi-dimensional spheres including learning data (black square mark) at locations where the learning data items are densely distributed. In a case where predictive fault indicator sensing target data (black circle mark) is input in the predictive fault indicator sensing mode, the abnormality calculation unit 26 calculates a distance from a position indicated by the predictive fault indicator sensing target data (black circle mark) to a surface of the closest cluster #1 or #2, as the abnormality Sd.

As described above, the predictive fault indicator determination unit 27 (refer to FIG. 2) determines the presence or absence of a predictive fault indicator by comparing the abnormality Sd with a predetermined threshold value. Generally, "0" is set as the threshold value. Therefore, in a case where a position indicated by the predictive fault indicator sensing target data (black circle mark) is included in the surface of the cluster #1 or #2 or the inside thereof, the abnormality Sd has a value of zero or a negative value, and thus it is determined that a predictive fault indicator is not sensed. In contrast, in a case where the abnormality Sd has a positive value, the predictive fault indicator sensing target data (black circle mark) is not included in either of the clusters, and thus it is determined that abnormal data, that is, a predictive fault indicator is sensed.

Here, effects of the present embodiment will be described with reference to FIG. 7. In the present embodiment, not only the frequency components w1, w2, . . . , and wn obtained through frequency analysis, but also the synchronization position representative values xyz (x, y, z), the synchronization temperature representative value T, and the synchronization angle representative value θ are used in the space where the learning unit 25 generates clusters. Therefore, in a case where positions, temperatures, and angles (attitude angles) of the X-ray tube 12 are different from each other, it cannot be said that clusters having the same frequency components are generated.

For example, in FIG. 7, the cluster #1 and the cluster #2 which are different from each other are formed at synchronization angle representative values (attitude angles of the X-ray tube 12) of about 0 degrees and about 60 degrees. This indicates that frequencies of vibration generated from the normal X-ray tube 12 are different from each other at attitude angles of about 0 degrees and about 60 degrees. In this case, in the present embodiment, in a case where an attitude angle of the X-ray tube 12 which is a predictive fault indicator sensing target is 0 degrees, when such vibration as is included in the cluster #2 is generated from the X-ray tube 12, this situation may be sensed as abnormality. In contrast, in a case where a space for generating clusters is formed of only the frequency components w1, w2, . . . , and wn, the situation cannot be sensed as abnormality.

In other words, in the present embodiment, a difference in abnormal noise can be sensed by taking into consideration a difference in a position, a temperature, and an attitude angle of the X-ray tube 12, and thus it is possible to sense a predictive fault indicator of the X-ray tube 12 with high accuracy.

FIG. 8 is a diagram illustrating an example of the entire process flow in the X-ray tube predictive fault indicator sensing device 11 according to the embodiment of the present invention. Processes in FIG. 8 and the subsequent drawings are performed by the central processing unit 113 (refer to FIG. 1) of the X-ray tube predictive fault indicator sensing device 11. In this case, it is assumed that an operation mode set by the mode setting unit 24 (refer to FIG. 4) has already been set to any one of the prohibition mode, the learning mode, and the predictive fault indicator sensing mode, and the set information is stored in the storage device 116 (refer to FIG. 1).

As illustrated in FIG. 8, first, the central processing unit 113 determines whether or not an operation mode set by the mode setting unit 24 is the prohibition mode (step S01). As a determination result, in a case where an operation mode is the prohibition mode (Yes in step S01), the central processing unit 113 does not perform any process, and finishes the process. In a case where an operation mode is not the prohibition mode (No in step S01), the central processing unit 113 further determines whether or not an operation mode is the learning mode (step S02).

As a determination result in step S02, in a case where an operation mode is the learning mode (Yes in step S02), the central processing unit 113 performs a learning process (step S03). In a case where an operation mode is not the learning mode (No in step S02), the central processing unit 113 determines whether or not the learning process has been performed, and an operation mode is the predictive fault indicator sensing mode (step S04).

As a determination result in step S04, in a case where the learning process has been performed, and an operation mode is the predictive fault indicator sensing mode (Yes in step S04), the central processing unit 113 performs a predictive fault indicator sensing process (step S05), and finishes the process. In a case where the learning process has not been performed, or an operation mode is not the predictive fault indicator sensing mode (No in step S04), the central processing unit 113 finishes the process.

The learning process in step S03 is a process for realizing the learning unit 25, and a more specific process flow will be described later with reference to FIG. 9. The predictive fault indicator sensing process in step S05 is a process for realizing the abnormality calculation unit 26 and the predictive fault indicator determination unit 27, and a more specific process flow will be described later with reference to FIG. 10.

FIG. 9 is a diagram illustrating an example of a specific process flow of the learning process. As illustrated in FIG. 9, in the learning process, first, the central processing unit 113 performs a representative value resetting process (step S11). The representative value resetting process is a process of resetting a position representative value, a temperature representative value, and an angle representative value respectively stored in the position representative value storage portion 2213, the temperature representative value storage portion 2223, and the angle representative value storage portion 2233, to zero, and a specific process flow thereof will be described later with reference to FIG. 11.

Next, the central processing unit 113 repeatedly performs processes from step S12 to step S17 by the same number as the number of learning samples. The number of learning samples is the number of series of time-series vibration data (vibration data corresponding to the number of FFT points) which is input for a frequency analysis process in the learning mode.

In the repeatedly performed processes from step S12 to step S17, first, the central processing unit 113 performs a measured data acquisition process until collecting of vibration data corresponding to the number of FFT points is completed (step S13 and step S14). The measured data acquisition process is a process of acquiring data such as three-axis accelerations, a temperature, and angular velocity measured by the acceleration sensor 131, the temperature sensor 132, and the gyro sensor 133 of the sensor unit 13, and calculating vibration data, a position representative value, a temperature representative value, and an angle representative value, and a specific process flow thereof will be described later with reference to FIG. 12.

If acquisition of vibration data corresponding to the number of FFT points is completed (Yes in step S14), the central processing unit 113 performs a representative value preservation process (step S15), and also performs a representative value resetting process (step S16). Here, the representative value preservation process is a process of accumulating a position representative value, a temperature representative value, and an angle representative value at a point at which acquisition of the vibration data is completed, in the position representative value history storage portion 2214, the temperature representative value history storage portion 2224, the angle representative value history storage portion 2234 of the state data acquisition unit 22 (refer to FIG. 3), respectively, in correlation with the time at that time, and a specific process flow thereof will be described later with reference to FIG. 13. A representative value resetting process in step S16 is the same as the representative value resetting process in step S11.

Successively, the central processing unit 113 repeatedly performs processes from step S18 to step S21 by the same number as the number of learning samples, and, in the repeatedly performed processes, performs an FFT process on vibration data of each learning sample (step S19) and performs a representative value acquisition process (step S20). Here, the FFT process is a process of performing frequency analysis on vibration data of each learning sample by using fast Fourier transform. The representative value acquisition process is a process of acquiring a position representative value, a temperature representative value, and an angle representative value at a time point closest to a time point at which final data of vibration data used for frequency analysis is acquired, as a synchronization position representative value, a synchronization temperature representative value, and a synchronization angle representative value, by referring to the position representative value history storage portion 2214, the temperature representative value history storage portion 2224, and the angle representative value history storage portion 2234. A specific process flow of the representative value acquisition process will be described later with reference to FIG. 14.

Through the repeatedly performed processes from step S18 to step S21, data such as the frequency analysis results w1, w2, . . . , and wn, corresponding to the number of learning samples, the synchronization position representative values xyz (x, y, z), the synchronization temperature representative value T, and the synchronization angle representative value θ can be obtained. In other words, a vector (w1, w2, . . . , wn, x, y, z, T, θ) of learning data corresponding to the number of learning samples is generated. Therefore, the central processing unit 113 performs cluster analysis on the vector (w1, w2, . . . , wn, x, y, z, T, θ) of learning data corresponding to the number of learning samples, calculates a cluster radius and centroid coordinates with respect to a generated cluster (step S22), and finishes the learning process.

In the cluster analysis in step S21, the cluster analysis may be performed not only on the vector of learning data generated through the repeatedly performed processes from step S18 to step S21 but also on a vector of learning data obtained from the same X-ray tube 12 in the past.

FIG. 10 is a diagram illustrating an example of a specific process flow of the predictive fault indicator sensing process. As illustrated in FIG. 10, in the predictive fault indicator sensing process, first, the central processing unit 113 performs a representative value resetting process (step S31). The representative value resetting process is the same as the representative value resetting process (step S11) in the learning process in FIG. 9, and a specific process flow thereof will be described later with reference to FIG. 11.

Hereinafter, processes from step S32 to step S37 are the same as the processes from step S12 to step S17 except that the number of learning samples is replaced with the number of sensing target samples in step S12 and step S17 in the learning process illustrated in FIG. 9, and thus a description thereof will be omitted. The number of sensing target samples is the number of series of time-series vibration data (vibration data corresponding to the number of FFT points) which is input for a frequency analysis process in the predictive fault indicator sensing mode.

Successively, the central processing unit 113 repeatedly performs processes from step S38 to step S42 by the same number as the number of sensing target samples, and, in the repeatedly performed processes, performs an FFT process on vibration data of each sensing target sample (step S39), performs a representative value acquisition process (step S40), further performs an abnormality calculation process (step S41), and finishes the predictive fault indicator sensing process.

Here, the FFT process in step S39 and the representative value acquisition process in step S40 are respectively the same as the FFT (step S19) and the representative value acquisition process (step S20) in the learning process illustrated in FIG. 9. Therefore, as results of the processes, the vector (w1, w2, . . . , wn, x, y, z, T, θ) of the predictive fault indicator sensing target data is generated. In the abnormality calculation process (step S41), a distance between a position indicated by the vector (w1, w2, . . . , wn, x, y, z, T, θ) of the predictive fault indicator sensing target data and a position of the cluster generated in the learning process (refer to FIG. 8) is obtained in a (n+5)-dimensional vector space, and the abnormality shown in Equation (3) is calculated. A specific process flow of the abnormality calculation process will be described later with reference to FIG. 15.

In the above-described way, if abnormalities are calculated for respective samples corresponding to the number of sensing targets, the central processing unit 113 performs a threshold value determination process (step S43), and outputs results thereof as predictive fault indicator sensing data. In the threshold value determination process, the abnormality calculated in the abnormality calculation process (step S41) is compared with a predetermined threshold value, and thus it is determined whether or not a predictive fault indicator is sensed, but, as a determination reference in this case, various references may be used. For example, if a single abnormality more than a predetermined threshold value is just sensed, it may be determined that a predictive fault indicator is sensed, and, alternatively, for example, if five or more abnormalities more than a predetermined threshold value are sensed, it may be determined that a predictive fault indicator is sensed.

FIG. 11 is a diagram illustrating an example of a specific process flow of the representative value resetting process. As illustrated in FIG. 11, in the representative value resetting process, first, the central processing unit 113 resets the position representative values (xa, ya, za) stored in the position representative value storage portion 2213 (refer to FIG. 3) and the number of samples Na to zero (step S111). Successively, the central processing unit 113 resets the temperature representative value Ta stored in the temperature representative value storage portion 2223 and the number of samples Na to zero (step S112), resets the angle representative value θa stored in the angle representative value storage portion 2233 and the number of samples Na to zero (step S113), and finishes the representative value resetting process.

FIG. 12 is a diagram illustrating an example of a specific process flow of the measured data acquisition process. As illustrated in FIG. 12, in the measured data acquisition process, three-axis accelerations, angular velocity, and a temperature (casing temperature) are acquired at different timings. In this example, since vibration data is calculated by using three-axis accelerations, a timing for acquiring three-axis accelerations may have an interval of, for example, about 10 μs, but a timing for acquiring a temperature may have an interval of, for example, 1 sec.

First, the central processing unit 113 determines whether or not a three-axis acceleration acquisition timing arrives, and acquires three-axis accelerations measured by the acceleration sensor 131 (step S52) in a case where the three-axis acceleration acquisition timing arrives (Yes in step S51). Next, the central processing unit 113 calculates the vibration data Dv on the basis of the three-axis accelerations, and stores the vibration data Dv in the recording device 115 along with the time at that time (step S53). The central processing unit 113 calculates the present position data (xc, yc, zc) at that time on the basis of the three-axis accelerations, and stores the data in the present position storage portion 2211 along with the time at that time (step S54). The central processing unit 113 calculates the position representative values (xa, ya, za) and the number of samples Na by using the above Equations (1) and (2), and stores the values in the position representative value storage portion 2213 along with the time at that time (step S55).

On the other hand, in a case where the three-axis acceleration acquisition timing does not arrive (No in step S51), the central processing unit 113 skips processes in steps S52 to S55, and proceeds to a determination process in step S56.

Next, the central processing unit 113 determines whether or not a temperature acquisition timing arrives, acquires the temperature data Dt of the casing of the X-ray tube 12, measured by the temperature sensor 132 (step S57) in a case where the temperature acquisition timing arrives (Yes in step S56), and stores the acquired temperature data Dt in the present temperature storage portion 2221 along with the time at that time (step S58). The central processing unit 113 calculates the temperature representative value Ta and the number of samples Na by using equations such as Equations (1) and (2), and stores the values in the temperature representative value storage portion 2223 along with the time at that time (step S59).

On the other hand, in a case where the temperature acquisition timing does not arrive (No in step S56), the central processing unit 113 skips processes in steps S57 to S59, and proceeds to a determination process in step S60.

Next, the central processing unit 113 determines whether or not an angular velocity acquisition timing arrives, acquires angular velocity measured in the gyro sensor 133 (step S61) in a case where the angular velocity acquisition timing arrives (Yes in step S60), calculates the present angle data Da at this time on the basis of the acquired angular velocity, and stores the acquired data in the present angle storage portion 2231 along with the time at that time (step S62). The central processing unit 113 calculates the angle representative value θa and the number of samples Na by using equations such as Equations (1) and (2), and stores the values in the angle representative value storage portion 2233 along with the time at that time (step S63). Next, the central processing unit 113 finishes the measured data acquisition process.

On the other hand, in a case where the angular velocity acquisition timing does not arrive (No in step S60), the central processing unit 113 skips processes in steps S61 to S63, and finishes the measured data acquisition process.

In the above-described measured data acquisition process, the central processing unit 113 acquires three-axis accelerations from the sensor unit 13, and calculates vibration data and position data on the basis of the three-axis accelerations, but, as illustrated in FIG. 2, the signal processing portion 135 of the sensor unit 13 may calculate and output the vibration data Dv (vibration data output portion 1351), and may calculate and output the position data Dp (position data output portion 1352). Similarly, the signal processing portion 135 of the sensor unit 13 may calculate and output the angel data Da on the basis of angular velocity (angle data output portion 1354).

FIG. 13 is a diagram illustrating an example of a specific process flow of the representative value preservation process. The representative value preservation process is performed when acquisition of unit time-series vibration data (vibration data corresponding to the number of FFT points) required in frequency analysis is completed, as illustrated in FIGS. 9 and 10.

As illustrated in FIG. 13, in the representative value preservation process, the central processing unit 113 saves the position representative values (xa, ya, za) stored in the position representative value storage portion 2213 at that point in the position representative value history storage portion 2214 along with the time at that time (step S151). Next, the central processing unit 113 saves the temperature representative value Ta stored in the temperature representative value storage portion 2223 at that point in the temperature representative value history storage portion 2224 along with the time at that time (step S152). Next, the central processing unit 113 saves the angle representative value θa stored in the angle representative value storage portion 2233 at that point in the angle representative value history storage portion 2234 along with the time at that time (step S153), and finishes the representative value preservation process.

Through the above-described representative value preservation process, the position representative values (xa, ya, za), the temperature representative value Ta, and the angle representative value θa respectively stored in the position representative value history storage portion 2214, the temperature representative value history storage portion 2224, and the angle representative value history storage portion 2234 can be said to be used as representative values synchronized with at the time point t at which the representative value preservation process is performed when acquisition of unit time-series vibration data (vibration data corresponding to the number of FFT points) required in frequency analysis is completed.

FIG. 14 is a diagram illustrating an example of a specific process flow of the representative value acquisition process. As illustrated in FIGS. 9 and 10, the representative value acquisition process (steps S20 and S40) is performed after the FFT process (steps S19 and S39).

In the representative value acquisition process illustrated in FIG. 14, first, the central processing unit 113 acquires a time point t correlated with the final vibration data among vibration data items used for the previous FFT process (step S201). Next, the central processing unit 113 extracts position representative values (xa, ya, za) correlated with a time point closest to the time point t from the position representative value history storage portion 2214, as synchronization position representative values (x(t), y(t), z(t)) (step S202). Next, the central processing unit 113 extracts a temperature representative value Ta correlated with a time point closest to the time point t from the temperature representative value history storage portion 2224, as a synchronization temperature representative value T(t) (step S203). Next, the central processing unit 113 extracts an angle representative value θa correlated with a time point closest to the time point t from the angle representative value history storage portion 2234, as a synchronization angle representative value θ(t) (step S204), and finishes the representative value acquisition process.

FIG. 15 is a diagram illustrating an example of a specific process flow of the abnormality calculation process. In the abnormality calculation process, with respect to a (n+5)-dimensional vector formed of the frequency components $w1(t), w2(t), \ldots,$ and wn(t), the synchronization position representative values x(t), y(t), and z(t), the synchronization temperature representative value T(t), and the synchronization angle representative value θ(t) obtained through the FFT (FIG. 10: step S39) and the representative value acquisition process (FIG. 10: step S40) in the predictive fault indicator sensing process, distances from a position indicated by the vector to surfaces of the m clusters generated in the learning process (refer to FIG. 9) are calculated, and the minimum value is extracted from thereamong, and is used as abnormality.

Therefore, the central processing unit 113 repeatedly performs processes from step S71 to step S73 on all of the clusters (j=1 to m). In the repeatedly performed processes, a distance dj(t) from a position indicated by the vector (w1 (t), w2 (t), ..., wn(t), x(t), y(t), z(t), T(t), θ(t)) to the surface of the cluster j is calculated (step S72). The distance dj(t) is calculated by using the above Equations (3) to (7).

The central processing unit 113 calculates the minimum value of them distances dj (t) (where j=1 tom) in the processes from step S71 to step S73, as abnormality Sd(t) (step S74), and finishes the abnormality calculation process.

FIG. 16 is a diagram illustrating an example of a configuration of data stored in the recording device 115. As illustrated in FIG. 16, the recording device 115 stores mode table data 50, time-series vibration data 51, X-ray tube state data 52, frequency analysis data 53, learning data 55, predictive fault indicator sensing data 56, and the like.

The mode table data 50 is formed of a plurality of data sets, each set including a mode number 501, an upper limit of the number of times of imaging 502, and a lower limit of the number of times of imaging 503. Each data set corresponds to a single operation mode of the X-ray tube predictive fault indicator sensing device 11. Therefore, the mode setting unit 24 (refer to FIGS. 1 and 3) acquires the number of times of imaging from the X-ray tube 12, acquires a prohibition flag from the prohibition flag setting unit, and sets an operation mode by referring to the mode table data 50.

The time-series vibration data 51 is data obtained by storing the vibration data Dv output from the sensor unit 13 in the order of time, and is formed of a plurality of time-series data items, each data item including a time point 511 and vibration data 512 correlated with each other. The time-series vibration data 51 is frequency analysis target data, and is used by the frequency analysis unit 21.

The X-ray tube state data 52 is formed of position data 521, temperature data 522, and angle data 523, and is data storing the present values, position representative values, or the like of the position data Dp, the temperature data Dt, and the angle data Da output from the sensor unit 13. A more specific configuration of the position data 521 will be described later with reference to FIG. 17.

The frequency analysis data 53 is formed of a sampling frequency 531, the number of frequency analysis points 532, frequency analysis result data 533, and the like. Here, the sampling frequency 531 is data for defining a cycle for acquiring the vibration data 512, and the number of frequency analysis points 532 is data for defining the number of frequency components which are output through frequency analysis. The frequency analysis result data 533 is data generated by the frequency analysis unit 21, and a specific configuration thereof will be described later with reference to FIG. 18.

The learning data 55 is formed of the number of learning samples 551, the cluster number maximum value 552, cluster data 553, and the like. Here, the number of learning samples 551 is the number of series of time-series vibration data (vibration data corresponding to the number of FFT points) which is input when the learning unit 25 generates the cluster data 553. The cluster number maximum value is the maximum value of the number of clusters when the learning unit 25 generates clusters. The cluster data 553 is generated by the learning unit 25, and a specific configuration thereof will be described later with reference to FIG. 19.

The predictive fault indicator sensing data 56 is formed of the number of sensing target samples 561, an abnormality threshold value 562, predictive fault indicator determination result data 563, and the like. Here, the predictive fault indicator determination result data 563 is the number of series of time-series vibration data (vibration data corresponding to the number of FFT points) which is input when the abnormality calculation unit 26 calculates abnormality. The abnormality threshold value 562 is a threshold value for determining whether the abnormality Sd calculated by the abnormality calculation unit 26 is normal or abnormal. The predictive fault indicator determination result data 563 is generated by the predictive fault indicator determination unit 27, and a specific configuration thereof will be described later with reference to FIG. 20.

FIG. 17 is a diagram illustrating an example of a specific configuration of the position data 521 included in the X-ray tube state data 52. As illustrated in FIG. 17, the position data 521 is formed of present position data 5211, position representative value data 5212, position representative value history data 5213, and the like. The present position data 5211 is configured to include the present time, and coordinate values (xc, yc, zc) of the present position, and the position representative value data 5212 is configured to include the present time, and the present position representative values (xc, yc, zc) and the number of samples (Na) at that time.

Whenever a frequency analysis completion flag of frequency analysis completion notification data 54 is set to ON in the frequency analysis unit 21, the position representative value history data 5213 is accumulated data by correlating the position representative values (xa, ya, za) stored as the position representative value data 5212 at that time, with a frequency analysis completion time point. In other words, the position representative value history data 5213 is formed of a completion time point (t(i)) which each frequency analysis completion time point, and a plurality of position representative values (xa(i), ya(i), za(i)) synchronized with the time point.

Here, the present position data 5211 is data stored in the present position storage portion 2211 described in FIG. 3; the position representative value data 5212 is data stored in the position representative value storage portion 2213 described in FIG. 3; and the position representative value history data 5213 is data stored in the position representative value history storage portion 2214 described in FIG. 3.

Specific configurations of the temperature data 522 and the angle data 523 included in the X-ray tube state data 52 (refer to FIG. 16) are similar to the specific configuration of the position data 521, and thus a description thereof will be omitted here.

FIG. 18 is a diagram illustrating an example of a specific configuration of the frequency analysis result data 533 included in the frequency analysis data 53. As illustrated in FIG. 18, the frequency analysis result data 533 is formed of unit analysis result data items corresponding to the number of learning samples or the number of sensing target samples, and each of the unit analysis result data items includes a frequency analysis completion time point, a plurality of frequency component data items, the synchronization position representative values (xa, ya, za), the synchronization temperature representative value (Ta), and the synchronization angle representative value (θa). In this case, each of the frequency component data items is constituted of data such as a frequency, power, and a phase.

The frequency analysis result data 533 obtained in the learning mode is used to generate a cluster in the learning unit 25, and the frequency analysis result data 533 obtained in the predictive fault indicator sensing mode is used to calculate the abnormality Sd in the abnormality calculation unit 26.

FIG. 19 is a diagram illustrating an example of a specific configuration of the cluster data 553 included in the learning data 55. As illustrated in FIG. 19, the cluster data 553 is formed of unit cluster data items corresponding to the number of clusters generated by the learning unit 25. Each of the unit cluster data items (data regarding the j-th cluster) is formed of cluster centroid coordinates (wj1, wj2, . . . , wjn, xj, yj, zj, Tj, θj), and a cluster radius rj.

FIG. 20 is a diagram illustrating an example of a specific configuration of the predictive fault indicator determination result data 563 included in the predictive fault indicator sensing data 56. As illustrated in FIG. 20, the predictive fault indicator determination result data 563 is formed of unit determination result data items corresponding to the number of sensing target samples 561. Each of the unit determination result data items is configured to include a time point, abnormality, and determination data. Here, the time point is a time point at which a predictive fault indicator sensing target sample is acquired, and the abnormality and the determination data are set on the basis of processing results in the abnormality calculation unit 26 and the predictive fault indicator determination unit 27.

In the above-described embodiment, the X-ray tube predictive fault indicator sensing device 11 performs cluster analysis not only on frequency analysis result data based on vibration data obtained by measuring vibration generated from the X-ray tube 12 but also on data such as a position, an attitude angle, and the temperature of the X-ray tube 12, so as to create cluster data. Also in a case of sensing a predictive fault indicator, a distance to the closest cluster surface, that is, the abnormality Sd is calculated by using not only frequency analysis result data based on vibration data obtained by measuring vibration generated from the X-ray tube 12 but also data including data such as a position, an attitude angle, and the temperature of the X-ray tube 12 at that time. Therefore, the abnormality Sd obtained in the above-described way causes the sensing accuracy of a predictive fault indicator to be increased compared with a case where abnormality (abnormal noise) of vibration data from the X-ray tube 12 is sensed by using clusters generated on the basis of only frequency analysis results of the vibration data. The reason is the same as described with reference to FIG. 7.

FIG. 21 is a diagram schematically illustrating an example of a configuration of an X-ray fluoroscopic imaging device 1 employing the X-ray tube predictive fault indicator sensing device 11 according to the embodiment of the present invention. As illustrated in FIG. 21, the X-ray fluoroscopic imaging device 1 is a device which captures an X-ray fluoroscopic image of a subject 7 by irradiating the subject 7 mounted on a table 3 with X-rays 6 from the X-ray tube 12 disposed over the subject, and sensing the X-rays 6 transmitted through the subject 7 with an X-ray detector 2 disposed under the table 3.

In this case, the sensor unit 13 is attached to the casing of the X-ray tube 12, and the sensor unit 13 is connected to the X-ray tube predictive fault indicator sensing device 11. The vibration data Dv, the position data Dp, the temperature data Dt, and the angel data Da measured by the sensor unit 13 are input to the X-ray tube predictive fault indicator sensing device 11. The X-ray tube 12 is also connected to the X-ray tube predictive fault indicator sensing device 11 (connection wirings are not illustrated), and the number-of-times-of-imaging data Dc regarding the X-ray tube 12 is input to the X-ray tube predictive fault indicator sensing device 11 from the X-ray tube 12.

The X-ray tube 12 is held at an X-ray tube support body 5, and is configured to be freely moved in a body axis direction of the subject 7 and a direction orthogonal to the body axis. The X-ray tube support body 5 is supported at the table 3 or a floor by columns 4, and is configured to be able to adjust a distance between the X-ray tube 12 and the subject 7 by expanding and contracting the columns 4. The X-ray tube support body 5 is configured to be able to incline or rotate the columns 4 centering on the body axis of the subject 7.

As described above, control for moving or inclining (rotating) the X-ray tube 12 is performed by an imaging control device 10. The imaging control device 10 controls an X-ray generation timing in the X-ray tube 12, and generates a fluoroscopic image of the subject 7 on the basis of intensity data of X-rays acquired by the X-ray detector 2.

FIG. 22 is a diagram schematically illustrating an example of a configuration of an X-ray CT device 1a employing the X-ray tube predictive fault indicator sensing device 11 according to the embodiment of the present invention. Fundamental constituent elements and functions of the X-ray CT device 1a are substantially the same as those of the X-ray fluoroscopic imaging device 1 illustrated in FIG. 21, but, details thereof are different from each other as follows. Hereinafter, only differences will be described.

In the X-ray CT device 1a, one corresponding to the X-ray tube support body 5 is referred to as a gantry 5a. The gantry 5a has a circular-ring shape, and the subject 7 mounted on the table 3 is put into a central part of the circular ring of the gantry 5a along the body axis thereof. The X-ray tube 12 and the X-ray detector 2 are supported in the gantry 5a to be disposed at positions opposite to each other centering on the body axis of the subject 7, and the gantry 5a is configured to be able to rotate the X-ray tube 12 and the X-ray detector 2 by 360 degrees centering on the body axis of the subject 7. Therefore, the X-ray tube 12 can irradiate the subject 7 with the X-rays 6 from all directions.

Therefore, the imaging control device 10 controls the X-ray tube 12 and the X-ray detector 2 so as to acquire X-ray fluoroscopic images of the subject 7 from all directions of 360 degrees, and generates tomographic images of a section perpendicular to the body axis of the subject 7 by using the X-ray fluoroscopic images of the subject 7 from all directions of 360 degrees. In other words, the X-ray CT device 1a is greatly different from the X-ray fluoroscopic imaging device 1 illustrated in FIG. 21 in that a simple fluoroscopic image of the subject 7 is not acquired, but a tomographic image of the subject 7 is acquired.

The X-ray detector 2 may not be disposed at a position on an opposite side to the X-ray tube 12, but may be disposed over the entire circumference of the circular ring of the gantry 5a. In this case, even when the X-ray tube 12 is rotated along the circular ring of the gantry 5a, the X-ray detector 2 is not rotated.

In the X-ray tube 12 of the above-described X-ray CT device 1a, both of a movement amount of a position and a change amount of an attitude angle are equal to or larger than in a case of the X-ray fluoroscopic imaging device 1 illustrated in FIG. 21. Therefore, the X-ray CT device 1a employs the X-ray tube predictive fault indicator sensing device 11, and can thus sense abnormality (abnormal noise) of vibration data of the X-ray tube 12 with high accuracy.

The present invention is not limited to the above-described embodiment, and further includes various modifications. The embodiment has been described in detail for better understanding of the present invention, and thus is not necessarily limited to including all of the above-described configurations. Some configurations of a certain embodiment may be replaced with some configurations of another embodiment, and some configurations or all configurations of another embodiment may be added to configurations of a certain embodiment.

REFERENCE SIGNS LIST

1 X-RAY FLUOROSCOPIC IMAGING DEVICE (X-RAY IMAGING DEVICE)
1a X-RAY CT DEVICE (X-RAY IMAGING DEVICE)
2 X-RAY DETECTOR
3 TABLE
4 COLUMN
5 X-RAY TUBE SUPPORT BODY
6 X-RAY
7 SUBJECT
10 IMAGING CONTROL DEVICE
11 X-RAY TUBE PREDICTIVE FAULT INDICATOR SENSING DEVICE
111 DISPLAY DEVICE
112 ALARM DEVICE
113 CENTRAL PROCESSING UNIT
114 OPERATION INPUT DEVICE
115 RECORDING DEVICE
116 STORAGE DEVICE
117 I/O PORT
12 X-RAY TUBE
121 X-RAY TUBE BULB
122 COIL
123 ROTATION ANODE
123a TARGET MEMBER
124 CATHODE
125 CONTROL UNIT
1251 NUMBER-OF-TIMES-OF-IMAGING COUNTING PORTION
13 SENSOR UNIT
131 ACCELERATION SENSOR
132 TEMPERATURE SENSOR
133 GYRO SENSOR
134 A/D CONVERTER
135 SIGNAL PROCESSING PORTION
1351 VIBRATION DATA OUTPUT PORTION
1352 POSITION DATA OUTPUT PORTION
1353 TEMPERATURE DATA OUTPUT PORTION
1354 ANGLE DATA OUTPUT PORTION
14 OPERATION CONSOLE
20 VIBRATION DATA ACQUISITION UNIT
21 FREQUENCY ANALYSIS UNIT
22 STATE DATA ACQUISITION UNIT
221 POSITION REPRESENTATIVE VALUE ACQUISITION SECTION
2211 PRESENT POSITION STORAGE PORTION
2212 POSITION REPRESENTATIVE VALUE CALCULATION PORTION
2213 POSITION REPRESENTATIVE VALUE STORAGE PORTION
2214 POSITION REPRESENTATIVE VALUE HISTORY STORAGE PORTION
222 TEMPERATURE REPRESENTATIVE VALUE ACQUISITION SECTION
2221 PRESENT TEMPERATURE STORAGE PORTION
2222 TEMPERATURE REPRESENTATIVE VALUE CALCULATION PORTION
2223 TEMPERATURE REPRESENTATIVE VALUE STORAGE PORTION
2224 TEMPERATURE REPRESENTATIVE VALUE HISTORY STORAGE PORTION
223 ANGLE REPRESENTATIVE VALUE ACQUISITION SECTION
2231 PRESENT ANGLE STORAGE PORTION
2232 ANGLE REPRESENTATIVE VALUE CALCULATION PORTION
2233 ANGLE REPRESENTATIVE VALUE STORAGE PORTION
2234 ANGLE REPRESENTATIVE VALUE HISTORY STORAGE PORTION
23 PROHIBITION FLAG SETTING UNIT
24 MODE SETTING UNIT
25 LEARNING UNIT
251 DEMULTIPLEXER
252 CLUSTER DATA GENERATION SECTION
253 MULTIPLEXER
26 ABNORMALITY CALCULATION UNIT
261 DEMULTIPLEXER
262 DISTANCE CALCULATION SECTION
263 MINIMUM VALUE EXTRACTION SECTION
27 PREDICTIVE FAULT INDICATOR DETERMINATION UNIT

The invention claimed is:

1. An X-ray tube predictive fault indicator sensing device comprising:
a mode setting unit that sets any one of operation modes including a prohibition mode, a learning mode, and a predictive fault indicator sensing mode;
a vibration data acquisition unit that acquires vibration data regarding vibration generated from an X-ray tube, and outputs a vibration data acquisition completion notification whenever the number of acquired vibration data items reaches multiples of a predetermined number of data items used for frequency analysis performed once;
a frequency analysis unit that performs the frequency analysis on each of vibration data items of the predetermined number acquired by the vibration data acquisition unit;
a state data acquisition unit that acquires state data indicating an operation state of the X-ray tube, and synchronizes the acquired state date with a timing at which the vibration data acquisition completion notification output from the vibration data acquisition unit is received;
a learning unit that performs cluster analysis by using, as input data, a plurality of learning data items formed of frequency component data obtained through the frequency analysis in the frequency analysis unit and the state data synchronized by the state data acquisition unit in a case where the learning mode is set by the mode setting unit, and generates one or more cluster data items;
an abnormality calculation unit that calculates, as abnormality, a minimum distance among distances to surfaces of respective clusters generated by the learning unit from a position indicated by predictive fault indicator sensing target data in a case where the predictive fault indicator sensing mode is set by the mode setting unit, the predictive fault indicator sensing target data being formed of the frequency component data obtained through the frequency analysis in the frequency analysis unit and the state data synchronized by the state data acquisition unit; and a predictive fault indicator determination unit that compares the abnormality calculated by the abnormality calculation unit with a predetermined threshold value so as to determine a predictive fault indicator.

2. The X-ray tube predictive fault indicator sensing device according to claim 1, wherein the state data acquired by the state data acquisition unit includes at least one of position data, attitude angle data, and temperature data of the X-ray tube.

3. The X-ray tube predictive fault indicator sensing device according to claim 1, wherein the synchronized state data is a mean value of the state data acquired by the state data acquisition unit while the vibration data items of the predetermined number are acquired by the vibration data acquisition unit.

4. The X-ray tube predictive fault indicator sensing device according to claim 1, wherein, on the basis of the number of times of imaging for the X-ray tube, transmitted from the X-ray tube, the mode setting unit sets the prohibition mode if the number of times of imaging is equal to or less than a first upper limit value, sets the learning mode if the number of times of imaging is more than the first upper limit value and is equal to or less than a second upper limit value greater than the first upper limit value, and sets the predictive fault indicator sensing mode if the number of times of imaging is more than the second upper limit value.

5. An X-ray tube predictive fault indicator sensing method, comprising:

a mode setting process of setting any one of operation modes including a prohibition mode, a learning mode, and a predictive fault indicator sensing mode;

a vibration data acquisition process of acquiring vibration data regarding vibration generated from an X-ray tube, and outputting a vibration data acquisition completion notification whenever the number of acquired vibration data items reaches multiples of a predetermined number of data items used for frequency analysis performed once;

a frequency analysis process of performing the frequency analysis on each of vibration data items of the predetermined number acquired through the vibration data acquisition process;

a state data acquisition process of acquiring state data indicating an operation state of the X-ray tube, and synchronizing the acquired state date with a timing at which the vibration data acquisition completion notification output through the vibration data acquisition process is received;

a learning process of performing cluster analysis by using, as input data, a plurality of learning data items formed of frequency component data obtained through frequency analysis in the frequency analysis process and the state data synchronized through the state data acquisition process in a case where the learning mode is set through the mode setting process, and generating one or more cluster data items;

an abnormality calculation process of calculating, as abnormality, a minimum distance among distances to surfaces of respective clusters generated through the learning process from a position indicated by predictive fault indicator sensing target data in a case where the predictive fault indicator sensing mode is set through the mode setting process, the predictive fault indicator sensing target data being formed of the frequency component data obtained through the frequency analysis in the frequency analysis process and the state data synchronized through the state data acquisition process; and a predictive fault indicator determination process of comparing the abnormality calculated through the abnormality calculation process with a predetermined threshold value so as to determine a predictive fault indicator.

6. The X-ray tube predictive fault indicator sensing method according to claim 5, wherein the state data acquired through the state data acquisition process includes at least one of position data, attitude angle data, and temperature data of the X-ray tube.

7. The X-ray tube predictive fault indicator sensing method according to claim 5, wherein the synchronized state data is a mean value of the state data acquired through the state data acquisition process while the vibration data items of the predetermined number are acquired through the vibration data acquisition process.

8. The X-ray tube predictive fault indicator sensing method according to claim 5, wherein, in the mode setting process, on the basis of the number of times of imaging for the X-ray tube, transmitted from the X-ray tube, the computer sets the prohibition mode if the number of times of imaging is equal to or less than a first upper limit value, sets the learning mode if the number of times of imaging is more than the first upper limit value and is equal to or less than a second upper limit value greater than the first upper limit value, and sets the predictive fault indicator sensing mode if the number of times of imaging is more than the second upper limit value.

9. An X-ray imaging device comprising the X-ray tube predictive fault indicator sensing device according to claim 1.

* * * * *